US011802103B2

(12) United States Patent
Pereira et al.

(10) Patent No.: US 11,802,103 B2
(45) Date of Patent: Oct. 31, 2023

(54) PROCESS OF MAKING CALCIUM ALPHA-KETOGLUTARATE

(71) Applicant: PONCE DE LEON HEALTH DESIGNATED ACTIVITY COMPANY, Drogheda (IE)

(72) Inventors: David Eugene Pereira, Apex, NC (US); Keshav Deo, Telangana (IN)

(73) Assignee: PONCE DE LEON HEALTH DESIGNATED ACTIVITY COMPANY, Drogheda (IE)

( * ) Notice: Subject to any disclaimer, the term of this patent is extended or adjusted under 35 U.S.C. 154(b) by 0 days.

(21) Appl. No.: 17/277,752

(22) PCT Filed: Sep. 23, 2019

(86) PCT No.: PCT/US2019/052498
§ 371 (c)(1),
(2) Date: Mar. 19, 2021

(87) PCT Pub. No.: WO2020/068705
PCT Pub. Date: Apr. 2, 2020

(65) Prior Publication Data
US 2021/0371368 A1 Dec. 2, 2021

Related U.S. Application Data

(60) Provisional application No. 62/736,320, filed on Sep. 25, 2018.

(51) Int. Cl.
*C07C 51/41* (2006.01)
(52) U.S. Cl.
CPC .......... *C07C 51/418* (2013.01); *C07C 51/412* (2013.01)
(58) Field of Classification Search
CPC ..... C07C 51/418; C07C 55/07; C07C 51/412; C07C 59/347
See application file for complete search history.

(56) References Cited

U.S. PATENT DOCUMENTS

| | | | |
|---|---|---|---|
| 2,776,926 A | 1/1957 | Sharpe | |
| 2,841,616 A * | 7/1958 | Berger | C07C 51/42 562/578 |
| 2,917,528 A | 12/1959 | Ramsey | |
| 3,875,304 A | 4/1975 | Hunt | |
| 4,045,585 A | 8/1977 | Appleman | |
| 4,632,921 A * | 12/1986 | Bauer | A61K 47/02 514/561 |
| 5,646,187 A | 7/1997 | Vinnars | |
| 6,306,430 B1 | 10/2001 | Sunvold | |
| 6,451,341 B1 | 9/2002 | Slaga | |
| 6,616,940 B2 | 9/2003 | Sunvold | |
| 6,649,654 B1 | 11/2003 | Karin | |
| 8,183,409 B2 * | 5/2012 | Christgau | C07C 51/412 562/571 |
| 8,367,121 B2 | 2/2013 | Mazzio | |
| 8,815,306 B2 | 8/2014 | Tripp | |
| 9,486,402 B2 | 11/2016 | Hung | |
| 9,511,057 B2 | 12/2016 | Tang | |
| 9,532,997 B2 | 1/2017 | Katajisto | |
| 2004/0053818 A1 | 3/2004 | Shah | |
| 2005/0106246 A1 | 5/2005 | Byrd | |
| 2007/0105942 A1 | 5/2007 | Heuer | |
| 2007/0135376 A1 | 6/2007 | Henderson | |
| 2008/0027139 A1 | 1/2008 | Pierzynowski | |
| 2008/0279786 A1 | 11/2008 | Cash | |
| 2009/0005437 A1 | 1/2009 | Gottlieb | |
| 2009/0291926 A1 | 11/2009 | Christgau | |
| 2010/0124537 A1 | 5/2010 | Kruszewska | |
| 2010/0150895 A1 | 6/2010 | Mazzio | |
| 2010/0260733 A1 | 10/2010 | Qi | |
| 2010/0280060 A1 | 11/2010 | Powers, III | |
| 2010/0303968 A1 | 12/2010 | Sunvold | |
| 2011/0039935 A1 | 2/2011 | Pierzynowski | |
| 2012/0177759 A1 | 7/2012 | Li | |
| 2014/0056862 A1 | 2/2014 | Greenberg | |
| 2014/0065099 A1 | 3/2014 | Alvarez | |
| 2014/0294855 A1 | 10/2014 | Rubin | |
| 2014/0350105 A1 | 11/2014 | D Agostino | |
| 2015/0174088 A1 | 6/2015 | Karau | |
| 2015/0297544 A1 | 10/2015 | Pierzynowski | |
| 2015/0328176 A1 | 11/2015 | Tedone | |
| 2015/0342854 A1 | 12/2015 | Shibuya | |
| 2016/0263092 A1 | 9/2016 | Wang | |
| 2016/0271200 A1 | 9/2016 | Morré | |
| 2016/0354334 A1 | 12/2016 | Huang | |
| 2017/0037043 A1 | 2/2017 | Liu | |

(Continued)

FOREIGN PATENT DOCUMENTS

| | | |
|---|---|---|
| CA | 3037968 | 4/2018 |
| CA | 3061381 | 11/2018 |

(Continued)

OTHER PUBLICATIONS

Bruice, P.Y., Table of Acids with Ka nd pKa values, Organic Chemistry, 5th Edition, Pearson Prentice Hall, 5 pages (Year: 2007).*
Dorwald, F. Z., Organic Synthesis: General Remarks, Side reactions in Organic synthesis, Wiley-VCH Veriag GmbH & co. KGaA,, 20 pages (Year: 2006).*
PCT Search Report prepared for PCT/US2019/052498, dated Dec. 18, 2019.
PCT/US2019/052498 International Search Report dated Dec. 18, 2019.
PCT/US2020/036987 International Search Report dated Aug. 31, 2020.
European Application No. 18790088 Partial Search Report dated Dec. 17, 2020.

(Continued)

*Primary Examiner* — Yate' K Cutliff
(74) *Attorney, Agent, or Firm* — Brannon Sowers & Cracraft PC

(57) ABSTRACT

Methods and processes for preparing calcium salts of alpha-ketoglutarate are described herein.

20 Claims, No Drawings

(56) References Cited

U.S. PATENT DOCUMENTS

| | | | |
|---|---|---|---|
| 2020/0157630 A1 | 5/2020 | Narain | |
| 2020/0188327 A1 | 6/2020 | Kennedy | |

FOREIGN PATENT DOCUMENTS

| | | | |
|---|---|---|---|
| CN | 101759553 | 6/2010 | |
| CN | 102976927 | * 3/2013 | ............ C07C 51/41 |
| MX | 2017004010 | 2/2018 | |
| PL | 420099 | 7/2018 | |
| SU | 352881 | 9/1972 | |
| WO | 0021525 | 4/2000 | |
| WO | 2006066244 | 6/2006 | |
| WO | 2007122190 | 11/2007 | |
| WO | 2009005464 | 1/2009 | |
| WO | 2009030453 | 3/2009 | |
| WO | 2010112362 | 10/2010 | |
| WO | 2012143405 | 10/2012 | |
| WO | 2013160792 | 10/2013 | |
| WO | 2014116985 | 7/2014 | |
| WO | 2015123229 | 8/2015 | |
| WO | 2015171723 | 11/2015 | |
| WO | 2016003854 | 1/2016 | |
| WO | 2016015634 | 2/2016 | |
| WO | 2016019224 | 2/2016 | |
| WO | 2016161921 | 10/2016 | |
| WO | 2016200447 | 12/2016 | |
| WO | 2017008060 | 1/2017 | |
| WO | 2018064468 | 4/2018 | |
| WO | 2018200736 | 11/2018 | |
| WO | 2019038655 | 2/2019 | |
| WO | 2020068705 | 4/2020 | |
| WO | 2020086733 | 4/2020 | |
| WO | 2020252005 | 12/2020 | |
| WO | 2020252014 | 12/2020 | |
| WO | 2022006500 | 1/2022 | |

OTHER PUBLICATIONS

Massimino, S., Kearns, R. J., Loos, K. M., Burr, J., Park, J. S., Chew, B., . . . & Hayek, M. G. (2003). Effects of Age and Dietary β-Carotene on Immunological Variables in Dogs. Journal of veterinary internal medicine, 17(6), 835-842.

Mishur, R. J., Khan, M., Munkácsy, E., Sharma, L., Bokov, A., Beam, H., . . . & Rea, S. L. (2016). Mitochondrial metabolites extend lifespan. Aging cell, 15(2), 336-348.

Nickson, Frailty Syndrome. pp. 1-7 (2015); Abstract only.

Niemiec, T., Sikorska, J., Harrison, A., Szmidt, M., Sawosz, E., Wirth-Dzieciolowska, E., . . . & Pierzynowski, S. (2011). Alpha-ketoglutarate stabilizes redox homeostasis and improves arterial elasticity in aged mice. Journal of physiology and pharmacology, 62(1), 37.

Talpur, R., Vu, J., Bassett, R., Stevens, V., & Duvic, M. (2009). Phase I/II randomized bilateral half-head comparison of topical bexarotene 1% gel for alopecia areata. Journal of the American Academy of Dermatology, 61(4), 592-e1.

Xue, Q. L. (2011). The frailty syndrome: definition and natural history. Clinics in geriatric medicine, 27(1), 1.

Zdzisińska, B., Żurek, A., & Kandefer-Szerszeń, M. (2017). Alpha-ketoglutarate as a molecule with pleiotropic activity: well-known and novel possibilities of therapeutic use. Archivum immunologiae et therapiae experimentalis, 65(1), 21-36.

Acin-Perez, R., Hoyos, B., Zhao, F., Vinogradov, V., Fischman, D. A., Harris, R. A., . . . & Hammerling, U. (2010). Control of oxidative phosphorylation by vitamin A illuminates a fundamental role in mitochondrial energy homoeostasis. The FASEB Journal, 24(2), 627-636.

Bauer, J. H., Goupil, S., Garber, G. B., & Helfand, S. L. (2004). An accelerated assay for the identification of lifespan-extending interventions in Drosophila melanogaster. Proceedings of the National Academy of Sciences, 101(35), 12980-12985.

Berry, D. C., Jin, H., Majumdar, A., & Noy, N. (2011). Signaling by vitamin A and retinol-binding protein regulates gene expression to inhibit insulin responses. Proceedings of the National Academy of Sciences, 108(11), 4340-4345.

Bhattacharya, R., Kumar, D., Sugendran, K., Pant, S. C., Tulsawani, R. K., & Vijayaraghavan, R. (2001). Acute toxicity studies of α-Ketoglutarate: a promising antidote for cyanide poisoning. Journal of Applied Toxicology: An International Journal, 21(6), 495-499.

Bhattacharya, R., Gujar, N., Singh, P., Rao, P., & Vijayaraghavan, R. (2011). Toxicity of alpha-ketoglutarate following 14-days repeated oral administration in Wistar rats. Cellular and molecular biology, 57(2), 1543-49.

Birck, R., Zimmermann, E., Wassmer, S., Nowack, R., & van der Woude, F. J. (1999). Calcium ketoglutarate versus calcium acetate for treatment of hyperphosphataemia in patients on maintenance haemodialysis: a cross-over study. Nephrology, dialysis, transplantation: official publication of the European Dialysis and Transplant Association-European Renal Association, 14(6), 1475-1479.

Blomqvist, B. I., Hammarqvist, F., von der Decken, A., & Wernerman, J. (1995). Glutamine and α-ketoglutarate prevent the decrease in muscle free glutamine concentration and influence protein synthesis after total hip replacement. Metabolism, 44(9), 1215-1222.

Bolster et al., AMP-activated Protein Kinase Suppresses Protein Synthesis in Rat Skeletal Muscle Through Down-Regulated Mammalian Target of Rapamycin (mTOR) Signaling. J Biol Chem 277(27): 23977-23980.

Bro, S., Rasmussen, R. A., Handberg, J., Olgaard, K., & Feldt-Rasmussen, B. (1998). Randomized crossover study comparing the phosphate-binding efficacy of calcium ketoglutarate versus calcium carbonate in patients on chronic hemodialysis. American journal of kidney diseases, 31(2), 257-262.

Bunik, V. I., Denton, T. T., Xu, H., Thompson, C. M., Cooper, A. J., & Gibson, G. E. (2005). Phosphonate analogues of α-ketoglutarate inhibit the activity of the α-ketoglutarate dehydrogenase complex isolated from brain and in cultured cells. Biochemistry, 44(31), 10552-10561.

Calixto, M. C., Lintomen, L., André, D. M., Leiria, L. O., Ferreira, D., Lellis-Santos, C., . . . & Antunes, E. (2013). Metformin attenuates the exacerbation of the allergic eosinophilic inflammation in high fat-diet-induced obesity in mice. PloS one, 8(10), e76786.

Chai, M., Jiang, M., Vergnes, L., Fu, X., de Barros, S. C., Jiao, J., . . . & Huang, J. (2018). Hair regeneration by small molecules that activate autophagy. Available at SSRN 3188356.

Chen, L., & Khillan, J. S. (2010). A novel signaling by vitamin A/retinol promotes self renewal of mouse embryonic stem cells by activating PI3K/Akt signaling pathway via insulin-like growth factor-1 receptor. Stem cells, 28(1), 57-63.

Chen, B. H., Marioni, R. E., Colicino, E., Peters, M. J., Ward-Caviness, C. K., Tsai, P. C., . . . & Horvath, S. (2016). DNA methylation-based measures of biological age: meta-analysis predicting time to death. Aging (Albany NY), 8(9), 1844.

Chin, R. M., Fu, X., Pai, M. Y., Vergnes, L., Hwang, H., Deng, G., . . . & Huang, J. (2014). The metabolite α-ketoglutarate extends lifespan by inhibiting ATP synthase and TOR. Nature, 510(7505), 397-401.

Darzynkiewicz, Z., Zhao, H., Halicka, H. D., Li, J., Lee, Y. S., Hsieh, T. C., & Wu, J. M. (2014). In search of antiaging modalities: evaluation of mTOR-and ROS/DNA damage-signaling by cytometry. Cytometry Part A, 85(5), 386-399.

Filip, Pierzynowski, Lindegard, Wernerman, Haratym-Maj, & Podgurniak. (2007). Alpha-ketoglutarate decreases serum levels of C-terminal cross-linking telopeptide of type I collagen (CTX) in postmenopausal women with osteopenia: six-month study. International journal for vitamin and nutrition research, 77(2), 89-97.

Gao, Z., Zuberi, A., Quon, M. J., Dong, Z., & Ye, J. (2003). Aspirin inhibits serine phosphorylation of insulin receptor substrate 1 in tumor necrosis factor-treated cells through targeting multiple serine kinases. Journal of Biological Chemistry, 278(27), 24944-24950.

Gibellini, L., Bianchini, E., De Biasi, S., Nasi, M., Cossarizza, A., & Pinti, M. (2015). Natural compounds modulating mitochondrial functions. Evidence-Based Complementary and Alternative Medicine, 2015.

(56) References Cited

OTHER PUBLICATIONS

Gomes, A. P., Duarte, F. V., Nunes, P., Hubbard, B. P., Teodoro, J. S., Varela, A. T., . . . & Rolo, A. P. (2012). Berberine protects against high fat diet-induced dysfunction in muscle mitochondria by inducing SIRT1-dependent mitochondrial biogenesis. Biochimica et Biophysica Acta (BBA)-Molecular Basis of Disease, 1822(2), 185-195.

Hou, Y., Wang, L., Ding, B., Liu, Y., Zhu, H., Liu, J., . . . & Wu, G. (2010). Dietary α-ketoglutarate supplementation ameliorates intestinal injury in lipopolysaccharide-challenged piglets. Amino acids, 39(2), 555-564.

International Application No. PCT/US2018/029455 International Search Report and Written Opinion dated Aug. 27, 2018.

Jeppsson, A., Ekroth, R., Friberg, P., Kirnö, K., Milocco, I., Nilsson, F. N., . . . & Jan Wernerman, M. D. (1998). Renal effects of α-ketoglutarate early after coronary operations. The Annals of thoracic surgery, 65(3), 684-690.

Kenyon, C. J. (2010). The genetics of ageing. Nature, 464(7288), 504-512.

Kjellman, U. W., Björk, K., Ekroth, R., Karlsson, H., Jagenburg, R., Nilsson, F. N., . . . & Wernerman, J. (1997). Addition of α-ketoglutarate to blood cardioplegia improves cardioprotection. The Annals of thoracic surgery, 63(6), 1625-1633.

Kjellman, U., Björk, K., Ekroth, R., Karlsson, H., Nilsson, F., Svensson, G., . . . & Wernerman, J. (1995). α-Ketoglutarate for myocardial protection in heart surgery. The Lancet, 345(8949), 552-553.

Kumar, S., & Lombard, D. B. (2016). Finding Ponce de Leon's pill: challenges in screening for anti-aging molecules. F1000Research, 5.

Kuo, C. L., Chi, C. W., & Liu, T. Y. (2004). The anti-inflammatory potential of berberine in vitro and in vivo. Cancer letters, 203(2), 127-137.

LeBrasseur, N. K., Kelly, M., Tsao, T. S., Farmer, S. R., Saha, A. K., Ruderman, N. B., & Tomas, E. (2006). Thiazolidinediones can rapidly activate AMP-activated protein kinase in mammalian tissues. American Journal of Physiology-Endocrinology and Metabolism, 291(1), E175-E181.

Liu, L. Z., Cheung, S. C., Lan, L. L., Ho, S. K., Xu, H. X., Chan, J. C., & Tong, P. C. (2010). Berberine modulates Insulin signaling transduction in insulin-resistant cells. Molecular and cellular endocrinology, 317(1-2), 148-153.

Liu, B., Li, W., Chang, Y., Dong, W., & Ni, L. (2006). Extraction of berberine from rhizome of Coptis chinensis Franch using supercritical fluid extraction. Journal of Pharmaceutical and Biomedical Analysis, 41(3), 1056-1060.

Long, A. N., Owens, K., Schlappal, A. E., Kristian, T., Fishman, P. S., & Schuh, R. A. (2015). Effect of nicotinamide mononucleotide on brain mitochondrial respiratory deficits in an Alzheimer's disease-relevant murine model. BMC neurology, 15(1), 1-14.

Mackenzie, E. D., Selak, M. A., Tennant, D. A., Payne, L. J., Crosby, S., Frederiksen, C. M., . . . & Gottlieb, E. (2007). Cell-permeating α-ketoglutarate derivatives alleviate pseudohypoxia in succinate dehydrogenase-deficient cells. Molecular and cellular biology, 27(9), 3282-3289.

McColl, G., Killilea, D. W., Hubbard, A. E., Vantipalli, M. C., Melov, S., & Lithgow, G. J. (2008). Pharmacogenetic analysis of lithium-induced delayed aging in Caenorhabditis elegans. Journal of Biological Chemistry, 283(1), 350-357.

Miller, R. A., Harrison, D. E., Astle, C. M., Baur, J. A., Boyd, A. R., De Cabo, R., . . . & Strong, R. (2011). Rapamycin, but not resveratrol or simvastatin, extends life span of genetically heterogeneous mice. The Journals of Gerontology: Series A, 66(2), 191-201.

Ming, M., Sinnett-Smith, J., Wang, J., Soares, H. P., Young, S. H., Eibl, G., & Rozengurt, E. (2014). Dose-dependent AMPK-dependent and independent mechanisms of berberine and metformin inhibition of mTORC1, ERK, DNA synthesis and proliferation in pancreatic cancer cells. PloS one, 9(12), e114573.

Mittal, G., Singh, T., Kumar, N., Bhatnagar, A., Tripathi, R. P., Tulsawani, R., . . . & Bhattacharya, R. (2010). Radiolabeling and dose fixation study of oral alpha-ketoglutarate as a cyanide antidote in healthy human volunteers. Clinical Toxicology, 48(6), 509-515.

Nair, A. B., & Jacob, S. (2016). A simple practice guide for dose conversion between animals and human. Journal of basic and clinical pharmacy, 7(2), 27.

Navrotskaya, V. V., Oxenkrug, G., Vorobyova, L. I., & Summergrad, P. (2012). Berberine prolongs life span and stimulates locomotor activity of Drosophila melanogaster. American journal of plant sciences, 3(7A), 1037.

Onken, B., & Driscoll, M. (2010). Metformin induces a dietary restriction-like state and the oxidative stress response to extend C. elegans healthspan via AMPK, LKB1, and SKN-1. PloS one, 5(1), e8758.

Pandey, M. K., Sung, B., Kunnumakkara, A. B., Sethi, G., Chaturvedi, M. M., & Aggarwal, B. B. (2008). Berberine modifies cysteine 179 of IκBα kinase, suppresses nuclear factor-κB-regulated antiapoptotic gene products, and potentiates apoptosis. Cancer research, 68(13), 5370-5379.

Park, D., Jeong, H., Lee, M. N., Koh, A., Kwon, O., Yang, Y. R., . . . & Ryu, S. H. (2016). Resveratrol induces autophagy by directly inhibiting mTOR through ATP competition. Scientific reports, 6(1), 1-11.

Parks, R. J., Fares, E., MacDonald, J. K., Ernst, M. C., Sinal, C. J., Rockwood, K., & Howlett, S. E. (2012). A procedure for creating a frailty index based on deficit accumulation in aging mice. Journals of Gerontology Series A: Biomedical Sciences and Medical Sciences, 67(3), 217-227.

PCT/US2018/029455 International Preliminary Report on Patentability dated Nov. 5, 2019.

Petkovich, D. A., Podolskiy, D. I., Lobanov, A. V., Lee, S. G., Miller, R. A., & Gladyshev, V. N. (2017). Using DNA methylation profiling to evaluate biological age and longevity interventions. Cell metabolism, 25(4), 954-960.

Riedel, E., Hampl, H., Steudle, V., & Nündel, M. (1996). Calcium alpha-ketoglutarate administration to malnourished hemodialysis patients improves plasma arginine concentrations. Mineral and electrolyte metabolism, 22(1-3), 119-122; Abstract Only.

Riedel, E., Nündel, M., & Hampl, H. (1996). α-Ketoglutarate application in hemodialysis patients improves amino acid metabolism. Nephron, 74(2), 261-265.

Rockwood, K., Blodgett, J. M., Theou, O., Sun, M. H., Feridooni, H. A., Mitnitski, A., . . . & Howlett, S. E. (2017). A frailty index based on deficit accumulation quantifies mortality risk in humans and in mice. Scientific reports, 7(1), 1-10.

Saiki, S., Sasazawa, Y., Imamichi, Y., Kawajiri, S., Fujimaki, T., Tanida, I., . . . & Hattori, N. (2011). Caffeine induces apoptosis by enhancement of autophagy via PI3K/Akt/mTOR/p70S6K inhibition. Autophagy, 7(2), 176-187.

Searle, S. D., Mitnitski, A., Gahbauer, E. A., Gill, T. M., & Rockwood, K. (2008). A standard procedure for creating a frailty index. BMC geriatrics, 8(1), 1-10.

Selman, C., Lingard, S., Choudhury, A. I., Batterham, R. L., Claret, M., Clements, M., . . . & Withers, D. J. (2008). Evidence for lifespan extension and delayed age-related biomarkers in insulin receptor substrate 1 null mice. The FASEB Journal, 22(3), 807-818.

Shukla, S., MacLennan, G. T., Fu, P., & Gupta, S. (2012). Apigenin attenuates insulin-like growth factor-I signaling in an autochthonous mouse prostate cancer model. Pharmaceutical research, 29(6), 1506-1517.

Robida-Stubbs, S., Glover-Cutter, K., Lamming, D. W., Mizunuma, M., Narasimhan, S. D., Neumann-Haefelin, E., . . . & Blackwell, T. K. (2012). TOR signaling and rapamycin influence longevity by regulating SKN-1/Nrf and DAF-16/FoxO. Cell metabolism, 15(5), 713-724.

Spindler, S. R., Mote, P. L., & Flegal, J. M. (2014). Lifespan effects of simple and complex nutraceutical combinations fed isocalorically to mice. Age, 36(2), 705-718.

Theou, O., Brothers, T. D., Rockwood, M. R., Haardt, D., Mitnitski, A., & Rockwood, K. (2013). Exploring the relationship between national economic indicators and relative fitness and frailty in middle-aged and older Europeans. Age and ageing, 42(5), 614-619.

Thompson, M. J. (2017). An epigenetic aging clock for dogs and wolves. Aging (Albany NY), 9(3), 1055.

(56) References Cited

OTHER PUBLICATIONS

Timmons, L., Court, D. L., & Fire, A. (2001). Ingestion of bacterially expressed dsRNAs can produce specific and potent genetic interference in Caenorhabditis elegans. Gene, 263(1-2), 103-112.

Uberti, F., Lattuada, D., Morsanuto, V., Nava, U., Bolis, G., Vacca, G., ... & Molinari, C. (2014). Vitamin D protects human endothelial cells from oxidative stress through the autophagic and survival pathways. The Journal of Clinical Endocrinology & Metabolism, 99(4), 1367-1374.

Wang, L., Hou, Y., Yi, D., Li, Y., Ding, B., Zhu, H., ... & Wu, G. (2015). Dietary supplementation with glutamate precursor α-ketoglutarate attenuates lipopolysaccharide-induced liver injury in young pigs. Amino acids, 47(7), 1309-1318.

Wang, Y. X., Kong, W. J., Li, Y. H., Tang, S., Li, Z., Li, Y. B., ... & Song, D. Q. (2012). Synthesis and structure-activity relationship of berberine analogues in LDLR up-regulation and AMPK activation. Bioorganic & medicinal chemistry, 20 (22), 6552-6558.

Wernerman, J., Hammarqvist, F., & Vinnars, E. (1990). α-Ketoglutarate and postoperative muscle catabolism. The Lancet, 335(8691), 701-703.

Whitehead, J. C., Hildebrand, B. A., Sun, M., Rockwood, M. R., Rose, R. A., Rockwood, K., & Howlett, S. E. (2014). A clinical frailty index in aging mice: comparisons with frailty index data in humans. Journals of Gerontology Series A: Biomedical Sciences and Medical Sciences, 69(6), 621-632.

Wirén, M., Permert, J., & örgen Larsson, J. (2002). α-ketoglutarate-supplemented enteral nutrition: effects on postoperative nitrogen balance and muscle catabolism. Nutrition, 18(9), 725-728.

Lee, Y. M., Lee, J. O., Jung, J. H., Kim, J. H., Park, S. H., Park, J. M., ... & Kim, H. S. (2008). Retinoic acid leads to cytoskeletal rearrangement through AMPK-Rac1 and stimulates glucose uptake through AMPK-p38 MAPK in skeletal muscle cells. Journal of Biological Chemistry, 283(49), 33969-33974.

Zhao, H., Halicka, H. D., Li, J., & Darzynkiewicz, Z. (2013). Berberine suppresses gero-conversion from cell cycle arrest to senescence. Aging (Albany NY), 5(8), 623.

Zhong, D., Xiong, L., Liu, T., Liu, X., Liu, X., Chen, J., ... & Zhou, W. (2009). The glycolytic inhibitor 2-deoxyglucose activates multiple prosurvival pathways through IGF1R. Journal of Biological Chemistry, 284(35), 23225-23233.

Zimmermann, E., Wassmer, S., & Steudle, V. (1996). Long-term treatment with calcium-alpha-ketoglutarate corrects secondary hyperparathyroidism. Mineral and electrolyte metabolism, 22(1-3), 196-199; Abstract Only.

Carretero, M., Gomez-Amaro, R. L., & Petrascheck, M. (2015). Pharmacological classes that extend lifespan of Caenorhabditis elegans. Frontiers in genetics, 6, 77.

Wyczalkowska-Tomasik, A., Czarkowska-Paczek, B., Zielenkiewicz, M., & Paczek, L. (2016). Inflammatory markers change with age, but do not fall beyond reported normal ranges. Archivum immunologiae et therapiae experimentalis, 64(3), 249-254.

Pieroni, L., Bastard, J. P., Piton, A., Khalil, L., Hainque, B., & Jardel, C. (2003). Interpretation of circulating C-reactive protein levels in adults: body mass index and gender are a must. Diabetes & metabolism, 29(2), 133-138.

Ridker, P. M., Rifai, N., Rose, L., Buring, J. E., & Cook, N. R. (2002). Comparison of C-reactive protein and low-density lipoprotein cholesterol levels in the prediction of first cardiovascular events. New England journal of medicine, 347(20), 1557-1565.

Tang, Y., Fung, E., Xu, A., & Lan, H. Y. (2017). C-reactive protein and ageing. Clinical and Experimental Pharmacology and Physiology, 44, 9-14.

Nojima, M., Iwasaki, M., Kasuga, Y., Yokoyama, S., Onuma, H., Nishimura, H., ... & Tsugane, S. (2018). Correlation between global methylation level of peripheral blood leukocytes and serum C reactive protein level modified by MTHFR polymorphism: a cross-sectional study. BMC cancer, 18(1), 1-10.

Tang, Y., Liang, P., Chen, J., Fu, S., Liu, B., Feng, M., ... & Lan, H. Y. (2018). The baseline levels and risk factors for high-sensitive C-reactive protein in Chinese healthy population. Immunity & Ageing, 15(1), 1-8.

Rifai, N., & Ridker, P. M. (2003). Population distributions of C-reactive protein in apparently healthy men and women in the United States: implication for clinical interpretation. Clinical chemistry, 49(4), 666-669.

Rea, I. M., Gibson, D. S., McGilligan, V., McNerlan, S. E., Alexander, H. D., & Ross, O. A. (2018). Age and age-related diseases: role of inflammation triggers and cytokines. Frontiers in immunology, 586.

Milan-Mattos, J. C., Anibal, F. D. F., Perseguini, N. M., Minatel, V., Rehder-Santos, P., Castro, C. A., ... & Catai, A. M. (2019). Effects of natural aging and gender on pro-inflammatory markers. Brazilian Journal of Medical and Biological Research, 52.

Ligthart, S., Marzi, C., Aslibekyan, S., Mendelson, M. M., Conneely, K. N., Tanaka, T., ... & Dehghan, A. (2016). DNA methylation signatures of chronic low-grade inflammation are associated with complex diseases. Genome biology, 17(1), 1-15.

Ajani, U. A., Ford, E. S., & Mokdad, A. H. (2004). Dietary fiber and C-reactive protein: findings from national health and nutrition examination survey data. The Journal of nutrition, 134(5), 1181-1185.

Myte, R., Sundkvist, A., Van Guelpen, B., & Harlid, S. (2019). Circulating levels of inflammatory markers and DNA methylation, an analysis of repeated samples from a population based cohort. Epigenetics, 14(7), 649-659.

Abu-Remaileh, M., Bender, S., Raddatz, G., Ansari, I., Cohen, D., Gutekunst, J., ... & Lyko, F. (2015). Chronic Inflammation Induces a Novel Epigenetic Program That Is Conserved in Intestinal Adenomas and in Colorectal CancerDNA Methylation Links Inflammation and Cancer. Cancer research, 75(10), 2120-2130.

Hamer, M., & Molloy, G. J. (2009). Association of C-reactive protein and muscle strength in the English Longitudinal Study of Ageing. Age, 31(3), 171-177.

De Almeida Roediger, M., de Fátima Nunes Marucci, M., Duim, E. L., Santos, J. L. F., de Oliveira Duarte, Y. A., & de Oliveira, C. (2019). Inflammation and quality of life in later life: findings from the health, well-being and aging study (SABE). Health and Quality of Life Outcomes, 17(1), 1-7.

Ma, Y., Griffith, J. A., Chasan-Taber, L., Olendzki, B. C., Jackson, E., Stanek III, E. J., ... & Ockene, I. S. (2006). Association between dietary fiber and serum C-reactive protein. The American journal of clinical nutrition, 83(4), 760-766.

Khera, A., McGuire, D. K., Murphy, S. A., Stanek, H. G., Das, S. R., Vongpatanasin, W., ... & de Lemos, J. A. (2005). Race and gender differences in C-reactive protein levels. Journal of the American college of cardiology, 46(3), 464-469.

Conole, E. L., Stevenson, A. J., Green, C., Harris, S. E., Maniega, S. M., Harris, M. A., ... & Cox, S. R. (2020). An epigenetic proxy of chronic inflammation outperforms serum levels as a biomarker of brain ageing. medRxiv.

Akbaraly, T. N., Hamer, M., Ferrie, J. E., Lowe, G., Batty, G. D., Hagger-Johnson, G., ... & Kivimäki, M. (2013). Chronic Inflammation as a determinant of future aging phenotypes. Cmaj, 185(16), E763-E770.

Custodero, C., Mankowski, R. T., Lee, S. A., Chen, Z., Wu, S., Manini, T. M., ... & Anton, S. D. (2018). Evidence-based nutritional and pharmacological interventions targeting chronic low-grade inflammation in middle age and older adults: A systematic review and meta-analysis. Ageing research reviews, 46, 42-59.

Au, B., Smith, K. J., Gariépy, G., & Schmitz, N. (2015). The longitudinal associations between C-reactive protein and depressive symptoms: evidence from the English Longitudinal Study of Ageing (ELSA). International journal of geriatric psychiatry, 30(9), 976-984.

Dörwald, F. Z. (2006). Organic Synthesis: General Remarks. Side Reactions in Organic Synthesis, Wiley-VCH, Veriag GmbH & co. KGaA., 20 pages.

Bruice, Paula Yurkanis. "Table o fAcids with Ka and pKa Values." Organic Chemistry, 5th ed. Pearson Prentice Hall, 5 pages, 2007.

(56) References Cited

OTHER PUBLICATIONS

Hogan, J. E. (1989). Hydroxypropylmethylcellulose sustained release technology. Drug Development and Industrial Pharmacy, 15(6-7), 975-999.

* cited by examiner

PROCESS OF MAKING CALCIUM ALPHA-KETOGLUTARATE

CROSS-REFERENCE TO RELATED APPLICATIONS

This application is a U.S. national application under 37 C.F.R. § 371(b) of International Application Serial No. PCT/US2019/052498 filed Sep. 23, 2019, which claims priority under 35 U.S.C. § 119(e) of U.S. Provisional Application Ser. No. 62/736,320, filed Sep. 25, 2018, the entire disclosures of which are incorporated herein by reference.

TECHNICAL FIELD

The invention described herein pertains to methods and processes for preparing calcium salts of alpha-ketoglutarate.

BACKGROUND

Alpha-ketoglutaric acid is an important biological molecule, which is a key intermediate in the Krebs cycle, a nitrogen transporter, and a co-substance in molecular oxidation. Alpha-ketoglutaric acid anion plays a key role in metabolism, mainly in aerobic organisms. A calcium salt of alpha-ketoglutarate (Ca-AKG) is an important source of alpha-ketoglutaric acid anion.

Alpha-Ketoglutarate anion (Formula 2, also known via the name of its acid 2-oxopentanedioic acid, 2-ketoglutaric acid, 2-oxoglutaric acid, or oxoglutaric acid depicted as Formula 1) is an intermediate in the Krebs cycle of eukaryotic organisms and is biosynthesized from isocitrate (in the Krebs cycle process) or L-glutamate (via alanine transaminase) in such organisms. Both alpha-ketoglutarate and its corresponding acid are commercially available, either via preparation from fermentation cultures (for example see U.S. Pat. No. 2,776,926) or chemical synthesis from closely related compounds.

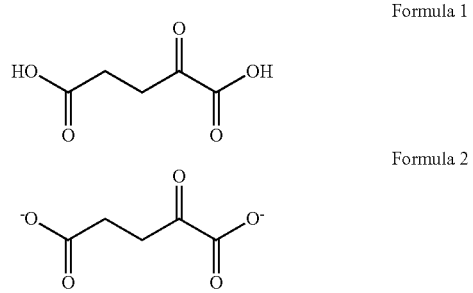

Formula 1

Formula 2

Consistent with its role in energy generation via the Krebs cycle, alpha-ketoglutarate is an important regulator of bioenergetics in cells and is implicated as an inhibitor of ATP synthase subunit β and an indirect inhibitor of the kinase mTOR, a consequence of partial inhibition of the mitochondrial electron transport chain.

Known methods for the synthesis of Ca-AKG from alpha-ketoglutaric acid require substantial purification of the final product which leads to the increased time and cost of the overall process. Accordingly, there is a need for discovery of novel methods for the synthesis of Ca-AKG from alpha-ketoglutaric acid with reduced formation of impurities.

SUMMARY OF THE INVENTION

Disclosed herein, in certain embodiments, are methods for making calcium alpha-ketoglutarate, the methods comprise a) contacting alpha-ketoglutaric acid with an alkali metal salt and water, thereby forming the corresponding bis salt of alpha-ketoglutarate; and b) contacting the bis salt of alpha-ketoglutarate with a calcium salt, thereby forming calcium alpha-ketoglutarate. Illustratively, the alkali metal salt is an alkali metal salt of an acid, where the conjugate acid of the alkali metal salt has at least one pKa from about 4 to about 12. Illustratively, the mixture of the alkali metal salt and water has a pH in the range from about 5.0 to about 11.9.

DETAILED DESCRIPTION

Unless otherwise defined, all technical and scientific terms used herein have the same meaning as commonly understood by one of ordinary skill in the art to which this disclosure pertains. Although methods and materials similar or equivalent to those described herein can be used in the practice or testing of the invention described herein, suitable methods and materials are described below. In case of conflict, the patent specification, including definitions, will control. In addition, the materials, methods, and examples are illustrative only and not intended to be limiting.

The phrase "pharmaceutically acceptable" is employed herein to refer to those compounds, materials, compositions, and/or dosage forms which are, within the scope of sound medical judgment, suitable for use in contact with the tissues of human beings and animals without unacceptable toxicity, irritation, allergic response, or other problem or complication, commensurate with a reasonable benefit/risk ratio.

As used herein, "alpha-ketoglutarate" or "AKG" comprises derivatives of alpha-ketoglutaratic acid (e.g., the derivatives set forth in MacKenzie, et al. (2007) Mol Cell Biol 27(9): 3282-3289)), analogues of alpha-ketoglutarate (e.g., phosphonate analogues (e.g., those recited in Bunik, et al. (2005) Biochemistry 44(31): 10552-61), esters of alpha-ketoglutarate (e.g., dimethyl alpha-ketoglutarate and octyl alpha-ketoglutarate), and various species specific analogues, e.g., human alpha-ketoglutarate, porcine alpha-ketoglutarate, murine alpha-ketoglutarate, bovine alpha-ketoglutarate, and the like.

Alpha-Ketoglutarate (AKG)

Described herein are processes of making calcium alpha-ketoglutarate.

In certain aspects, the disclosure provides compositions that comprise compounds (e.g. alpha-ketoglutarate salts) that are available for human consumption without FDA approval or generally recognized as safe (GRAS). Such compounds may be so classified because they are: a) present in the FDA SCOGS database and are generally recognized as safe by the U.S. Food and Drug Administration; or b) are derived from plants (for e.g. fruits, vegetables, herbs) present in traditional diets and so are recognized by the scientific community as safe for consumption. In some embodiments GRAS compounds are those compounds which are available for human consumption without FDA approval.

In some embodiments, alpha-ketoglutarate is provided as a monolithium salt, a dilithium salt, a monosodium salt, a disodium salt, a monopotassium salt, a dipotassium salt, or a mixed salt of lithium, sodium, or potassium, a calcium salt, or a zinc salt. In some embodiments, alpha-ketoglutarate is provided as a calcium salt. In further embodiments, the calcium salt of alpha-ketoglutarate is provided as anhydrous salt, monohydrate, or dihydrate. In yet further embodiments, alpha-ketoglutarate is provided as a mono- or di-valent salt with other cations described in the U.S. FDA *Orange Book*. Such cations include calcium, diolamine, lithium, lysine, magnesium, meglumine, olamine, tromethamine, and zinc.

Processes for Preparing Calcium Alpha-Ketoglutarate (Ca-AKG)

In one illustrative embodiment of the invention, described herein is a method for making calcium alpha-ketoglutarate, the method comprising:
   a) contacting alpha-ketoglutaric acid with an alkali metal salt of an acid and water, thereby forming a bis salt of alpha-ketoglutarate; and
   b) contacting the bis salt of alpha-ketoglutarate with a calcium salt and water, thereby forming calcium alpha-ketoglutarate;
   wherein the conjugate acid of the alkali metal salt of has a pKa from about 4 to about 12.

In another embodiment, described herein is a method for making calcium alpha-ketoglutarate, the method comprising:
   a) contacting alpha-ketoglutaric acid with an alkali metal salt of an acid and water to form a solution having a pH in the range from about 5 to about 11.9, thereby forming a bis salt of alpha-ketoglutarate; and
   b) contacting the bis salt of alpha-ketoglutarate with a calcium salt and water, thereby forming calcium alpha-ketoglutarate.

Several illustrative embodiments of the invention are described by the following enumerated clauses:

1. A method for making calcium alpha-ketoglutarate, the method comprising:
   a) contacting alpha-ketoglutaric acid with an alkali metal salt of an acid, where the conjugate acid of the alkali metal salt has at least one pKa from about 4 to about 12, thereby forming a bis salt of alpha-ketoglutarate; and
   b) contacting the bis salt of alpha-ketoglutarate with a calcium salt, thereby forming calcium alpha-ketoglutarate.

2. The method of clause 1 wherein the conjugate of the acid has at least one pKa from about 5 to about 12

3. The method of clause 1 wherein the conjugate of the acid has at least one pKa from about 5.5 to about 12.

4. The method of clause 1 wherein the conjugate of the acid has at least one pKa from about 5.5 to about 11.5.

5. The method of clause 1 wherein the conjugate of the acid has at least one pKa from about 6 to about 11.5.

6. The method of clause 1 wherein the conjugate of the acid has at least one pKa from about 6 to about 11.

7. A method for making calcium alpha-ketoglutarate, the method comprising:
   a) contacting alpha-ketoglutaric acid with an alkali metal salt of an acid and water to form a solution having a pH in the range from about 5 to about 11.9, thereby forming a bis salt of alpha-ketoglutarate; and
   b) contacting the bis salt of alpha-ketoglutarate with a calcium salt and water, thereby forming calcium alpha-ketoglutarate.

8. The method of clause 7 wherein the pH is in the range from about 5.3 to about 11.6.

9. The method of any one of the preceding clauses wherein the alpha-ketoglutaric acid is mixed with water.

10. The method of any one of the preceding clauses wherein the alpha-ketoglutaric acid and water mixture is prepared from or contains from about 0.05 to about 0.5 weight equivalents of alpha-ketoglutaric acid per one weight equivalent of water.

11. The method of any one of the preceding clauses wherein the alkali metal salt is mixed with water.

12. The method of clause 11 wherein the alkali metal salt and water mixture has a pH in the range from about 5 to about 11.9.

13. The method of clause 11 wherein the alkali metal salt and water mixture has a pH in the range from about 5.2 to about 11.6.

14. The method of clause 11 wherein the alkali metal salt and water mixture has a pH in the range from about 5.3 to about 11.5.

15. The method of clause 11 wherein the alkali metal salt and water mixture has a pH in the range from about 5.3 to about 8.4.

16. The method of any one of the preceding clauses wherein the alkali metal salt and water mixture is prepared from or contains from about 0.1 to about 0.35 weight equivalents of alkali metal salt per one weight equivalent of water.

17. The method of any one of the preceding clauses wherein the alkali metal salt is selected from the group consisting of lithium, sodium, and potassium salts of bicarbonate and carbonate, and combinations thereof.

18. The method of any one of the preceding clauses wherein the alkali metal salt includes sodium bicarbonate, sodium carbonate, or a mixture thereof.

19. The method of any one of the preceding clauses wherein the alkali metal salt includes sodium bicarbonate.

20. The method of any one of the preceding clauses wherein the sodium bicarbonate and water mixture contains from about 0.2 to about 0.3 weight equivalents of sodium bicarbonate per one weight equivalent of water.

21. The method of clause 20 wherein the sodium bicarbonate and water mixture contains from about 0.23 to about 0.28 weight equivalents of sodium bicarbonate per one weight equivalent of water.

22. The method of any one of the preceding clauses wherein the alkali metal salt includes sodium carbonate.

23. The method of clause 22 wherein the sodium carbonate and water mixture contains from about 0.05 to about 0.2 weight equivalents of sodium carbonate per one weight equivalent of water.

24. The method of clause 22 wherein the sodium carbonate and water mixture contains from about 0.1 to about 0.2 weight equivalents of sodium carbonate per one weight equivalent of water.

25. The method of any one of the preceding clauses wherein the alkali metal salt is added to the alpha-ketoglutaric acid to form a mixture having a pH of at least about 6.5, optionally after a predetermined period of time.

26. The method of clause 25 wherein the alkali metal salt is added to the alpha-ketoglutaric acid to form a mixture having a pH of at least about 7.0, optionally after a predetermined period of time.

27. The method of clause 25 wherein the alkali metal salt is added to the alpha-ketoglutaric acid to form a mixture having a pH of at least about 7.5, optionally after a predetermined period of time.

28. The method of clause 25 wherein the alkali metal salt is added to the alpha-ketoglutaric acid to form a mixture having a pH of at least about 8, optionally after a predetermined period of time.

29. The method of clause 25 wherein the alkali metal salt is added to the alpha-ketoglutaric acid to form a mixture having a pH of at least about 8.5, optionally after a predetermined period of time.

30. The method of clause 25 wherein the alkali metal salt is added to the alpha-ketoglutaric acid to form a mixture having a pH from about 6.5 to about 9, optionally after a predetermined period of time.

31. The method of clause 25 wherein the alkali metal salt is added to the alpha-ketoglutaric acid to form a mixture having a pH from about 6.5 to about 8.5, optionally after a predetermined period of time.

32. The method of any one of the preceding clauses wherein the alpha-ketoglutaric acid is from about 0.5 to about 3 weight equivalents per one weight equivalent of alkali metal salt.

33. The method of clause 32 wherein the alpha-ketoglutaric acid is from about 0.7 to about 0.9 weight equivalents per one weight equivalent of sodium bicarbonate.

34. The method of clause 32 wherein the alpha-ketoglutaric acid is from about 0.74 to about 0.88 weight equivalents per one weight equivalent of sodium bicarbonate.

35. The method of any one of the preceding clauses wherein the alpha-ketoglutaric acid is from about 1.0 to about 2.8 weight equivalents per one weight equivalent of sodium carbonate.

36. The method of clause 35 wherein the alpha-ketoglutaric acid is from about 1.1 to about 2.8 weight equivalents per one weight equivalent of sodium carbonate.

37. The method of clause 35 wherein the alpha-ketoglutaric acid is from about 1.1 to about 2.5 weight equivalents per one weight equivalent of sodium carbonate.

38. The method of clause 35 wherein the alpha-ketoglutaric acid is from about 1.1 to about 1.2 weight equivalents per one weight equivalent of sodium carbonate.

39. The method of any one of the preceding clauses wherein the alpha-ketoglutaric acid is contacted with the sodium bicarbonate and water mixture at about 50° C. or less.

40. The method of clause 39 wherein the alpha-ketoglutaric acid is contacted with the sodium bicarbonate and water mixture at about 40° C. or less.

41. The method of clause 39 wherein the alpha-ketoglutaric acid is contacted with the sodium bicarbonate and water mixture at about 35° C. or less.

42. The method of clause 39 wherein the alpha-ketoglutaric acid is contacted with the sodium bicarbonate and water mixture at about 30° C. or less.

43. The method of clause 39 wherein the alpha-ketoglutaric acid is contacted with the sodium bicarbonate and water mixture at about 25° C. or less.

44. The method of clause 39 wherein the alpha-ketoglutaric acid is contacted with the sodium bicarbonate and water mixture at about 10° C. to about 50° C.

45. The method of clause 39 wherein the alpha-ketoglutaric acid is contacted with the sodium bicarbonate and water mixture at about 10° C. to about 40° C.

46. The method of clause 39 wherein the alpha-ketoglutaric acid is contacted with the sodium bicarbonate and water mixture at about 10° C. to about 35° C.

47. The method of clause 39 wherein the alpha-ketoglutaric acid is contacted with the sodium bicarbonate and water mixture at about 10° C. to about 30° C.

48. The method of clause 39 wherein the alpha-ketoglutaric acid is contacted with the sodium bicarbonate and water mixture at about 10° C. to about 25° C.

49. The method of any one of the preceding clauses wherein the alpha-ketoglutaric acid and the sodium bicarbonate and water mixture is stirred for at least about 30 minutes.

50. The method of clause 49 wherein the alpha-ketoglutaric acid and the sodium bicarbonate and water mixture is stirred for at least about 1 hour.

51. The method of clause 49 wherein the alpha-ketoglutaric acid and the sodium bicarbonate and water mixture is stirred for at least about 2 hours.

52. The method of clause 49 wherein the alpha-ketoglutaric acid and the sodium bicarbonate and water mixture is stirred for at least about 3 hours.

53. The method of clause 49 wherein the alpha-ketoglutaric acid and the sodium bicarbonate and water mixture is stirred for at least about 4 hours.

54. The method of clause 49 wherein the alpha-ketoglutaric acid and the sodium bicarbonate and water mixture is stirred for about 30 minutes to about 6 hours or less.

55. The method of clause 49 wherein the alpha-ketoglutaric acid and the sodium bicarbonate and water mixture is stirred for about 1 hour to about 6 hours or less.

56. The method of clause 49 wherein the alpha-ketoglutaric acid and the sodium bicarbonate and water mixture is stirred for about 2 hour to about 6 hours or less.

57. The method of any one of the preceding clauses wherein the calcium salt is selected from the group consisting of calcium formate, calcium acetate, and calcium chloride.

58. The method of clause 57 wherein the calcium salt is calcium chloride.

59. The method of any one of the preceding clauses wherein the calcium salt is mixed with water.

60. The method of clause 59 wherein the calcium salt and water mixture is prepared from or contains from about 0.1 to about 1 weight equivalents of the calcium salt per one weight equivalent of water.

61. The method of clause 59 wherein the calcium chloride and water mixture contains from about 0.1 to about 0.6 weight equivalents of the calcium chloride per one weight equivalent of water.

62. The method of clause 59 wherein the calcium chloride and water mixture contains from about 0.2 to about 0.5 weight equivalents of the calcium chloride per one weight equivalent of water.

63. The method of clause 59 wherein the calcium chloride and water mixture contains from about 0.23 to about 0.4 weight equivalents of the calcium chloride per one weight equivalent of water.

64. The method of clause 59 wherein the calcium chloride and water mixture contains from about 0.2 to about 0.5 weight equivalents of the calcium chloride per one weight equivalent of water.

65. The method of any one of the preceding clauses wherein the calcium salt is from 0.5 to 2 weight equivalents per one weight equivalent of alpha-ketoglutaric acid.

66. The method of clause 64 wherein the calcium salt is from 0.75 to 2 weight equivalents per one weight equivalent of alpha-ketoglutaric acid.

67. The method of clause 64 wherein the calcium chloride is from about 0.75 to about 1.35 weight equivalents per one weight equivalent of alpha-ketoglutaric acid.

68. The method of clause 64 wherein the calcium chloride is from about 0.9 to about 1.1 weight equivalents per one weight equivalent of alpha-ketoglutaric acid.

69. The method of any one of the preceding clauses wherein the bis salt of alpha-ketoglutarate, such as the disodium alpha-ketoglutarate is contacted with the calcium salt and water mixture at about 40° C. to about 90° C.

70. The method of clause 69 wherein the bis alkali metal salt of alpha-ketoglutarate, such as the disodium alpha-ketoglutarate and the calcium salt and water mixture is stirred at about 65° C. to about 75° C.

71. The method of any one of the preceding clauses wherein the bis alkali metal salt of alpha-ketoglutarate, such as the disodium alpha-ketoglutarate and the calcium salt and water mixture is stirred for at least about 30 min.

72. The method of clause 71 wherein the bis alkali metal salt of alpha-ketoglutarate, such as the disodium alpha-ketoglutarate and the calcium salt and water mixture is stirred for at least about 1 hour.

73. The method of clause 71 wherein the bis alkali metal salt of alpha-ketoglutarate, such as the disodium alpha-ketoglutarate and the calcium salt and water mixture is stirred for at least about 2 hours.

74. The method of clause 71 wherein the bis alkali metal salt of alpha-ketoglutarate, such as the disodium alpha-ketoglutarate and the calcium salt and water mixture is stirred for at least about 4 hours.

75. The method of clause 71 wherein the bis alkali metal salt of alpha-ketoglutarate, such as the disodium alpha-ketoglutarate and the calcium salt and water mixture is stirred for at least about 5 hours.

76. The method of clause 71 wherein the bis alkali metal salt of alpha-ketoglutarate, such as the disodium alpha-ketoglutarate and the calcium salt and water mixture is stirred for about 30 minutes to about 5 hours or less.

77. The method of clause 71 wherein the bis alkali metal salt of alpha-ketoglutarate, such as the disodium alpha-ketoglutarate and the calcium salt and water mixture is stirred for about 1 hour to about 5 hours or less.

78. The method of clause 71 wherein the bis alkali metal salt of alpha-ketoglutarate, such as the disodium alpha-ketoglutarate and the calcium salt and water mixture is stirred for about 2 hours to about 5 hours or less.

79. The method of any one of the preceding clauses further comprising drying the calcium alpha-ketoglutarate.

80. The method of any one of the preceding clauses further comprising drying the calcium alpha-ketoglutarate to a moisture content of about 20% to about 5%.

81. The method of clause 80 comprising drying the calcium alpha-ketoglutarate to a moisture content of about 15% to about 5%.

82. The method of clause 80 comprising drying the calcium alpha-ketoglutarate to a moisture content of about 15% to about 8%.

83. The method of clause 80 comprising drying the calcium alpha-ketoglutarate to a moisture content of about 12% to about 8%.

84. The method of clause 80 comprising drying the calcium alpha-ketoglutarate to a moisture content of about 10% to about 8%.

85. The method of any one of the preceding clauses further comprising drying the calcium alpha-ketoglutarate, where the dried calcium alpha-ketoglutarate is less than 50% calcium alpha-ketoglutarate dihydrate.

86. The method of any one of the preceding clauses further comprising drying the calcium alpha-ketoglutarate, where the dried calcium alpha-ketoglutarate is at least 50% calcium alpha-ketoglutarate monohydrate.

87. A method for making calcium alpha-ketoglutarate, the method comprising:
   a) contacting alpha-ketoglutaric acid with a solution of sodium bicarbonate and water, thereby forming disodium alpha-ketoglutarate; and
   b) contacting the disodium alpha-ketoglutarate with a solution of calcium chloride and water, thereby forming calcium alpha-ketoglutarate;
   wherein the solution of sodium bicarbonate is prepared from about 0.27 weight equivalents of sodium bicarbonate per one weight equivalent of water;
   wherein the alpha-ketoglutaric acid is about 0.74 weight equivalents per one weight equivalent of sodium bicarbonate;
   wherein the alpha-ketoglutaric acid is contacted with the solution of sodium bicarbonate and water at about 10° C. to about 35° C., or at about 10° C. to about 25° C.;
   wherein the alpha-ketoglutaric acid and the solution of sodium bicarbonate and water is stirred for about 2 hours at about 10° C. to about 35° C., or at about 10° C. to about 25° C.;
   wherein the solution of calcium chloride is prepared from about 0.2 to about 0.5 weight equivalents of the calcium chloride per one weight equivalent of water;
   wherein the calcium chloride is about 0.95 weight equivalents per one weight equivalent of alpha-ketoglutaric acid;
   wherein the disodium alpha-ketoglutarate and the solution of calcium chloride is stirred for about 4 hours at 65° C. to 70° C.

88. A method for making calcium alpha-ketoglutarate, the method comprising:
   a) contacting alpha-ketoglutaric acid with a solution of sodium carbonate and water, thereby forming disodium alpha-ketoglutarate; and
   b) contacting the disodium alpha-ketoglutarate with a solution of calcium chloride and water, thereby forming calcium alpha-ketoglutarate;
   wherein the solution of sodium carbonate is prepared from about 0.18 weight equivalents of sodium carbonate per one weight equivalent of water;
   wherein the alpha-ketoglutaric acid is about 1.14 weight equivalents per one weight equivalent of sodium carbonate;
   wherein the alpha-ketoglutaric acid is contacted with the solution of sodium carbonate and water at about 10° C. to about 35° C., or at about 10° C. to about 25° C.;
   wherein the alpha-ketoglutaric acid and the solution of sodium carbonate and water is stirred for 2 hours at about 10° C. to about 35° C., or at about 10° C. to about 25° C.;
   wherein the solution of calcium chloride is prepared from about 0.2 to about 0.5 weight equivalents of the calcium chloride per one weight equivalent of water;
   wherein the calcium chloride is about 0.95 weight equivalent per one weight equivalent of alpha-ketoglutaric acid;
   wherein the disodium alpha-ketoglutarate and the solution of calcium salt and water is stirred for about 4 hours at 65° C. to 70° C.

It is to be understood that all weight equivalents of components, reactants, reagents, solvents, and the like, described herein are a description of the corresponding mole equivalents, each of which is obtained from the molecular weight of such components, reactants, reagents, solvents, and the like. In addition, it is to be understood that certain weight equivalents, such as weight equivalents of specific alkali metal salts to water can be converted to the corresponding weight equivalents of alternative alkali metal salts to water by accounting for the different molecular weights of the specific alkali metal salts and the alternative alkali metal salts. It is also to be understood that the same conversion between specific weight equivalents of alpha-ketoglutaric acid to water, or weight equivalents of alpha-ketoglutaric acid to alkali metal salts, or weight equivalents of calcium salts to water, or weight equivalents of calcium salts to alpha-ketoglutaric acid to alternatives, respectively, by accounting for the different molecular weights in each case.

For example, it is to be understood that all weight equivalents of alkali metal salts of acids described herein may also be represented as mole equivalents, such as in a mole ratio or a molar concentration. Illustratively, where the water mixture contains from about 0.1 to about 0.35 weight equivalents of sodium bicarbonate per one weight equivalent of water corresponds to about 1.2 to about 4.2 mmole equivalents of sodium bicarbonate, or sodium ion, per mL of water, or a sodium ion concentration range of about 1.2 to about 4.2 mmolar. It is to be further understood that the same range of mmole equivalents, or mmolar concentrations can be used with other alkali metal salts of acids or mixtures thereof, such as lithium bicarbonate, lithium carbonate, sodium carbonate, potassium bicarbonate, potassium carbonate, and the like described herein. It is to be further understood that the same range of mmole equivalents, or mmolar concentration used with other alkali metal salts of acids, such as lithium bicarbonate, lithium carbonate, sodium carbonate, potassium bicarbonate, potassium carbonate, and the like described herein, may be expressed as the corresponding weight equivalents.

Illustratively, the methods described herein include contacting alpha-ketoglutaric acid with a water mixture of potassium bicarbonate, where the water mixture contains from about 1.2 to about 4.2 mmole equivalents of potassium bicarbonate, or potassium ion, per mL of water, or a potassium ion concentration range of about 1.2 to about 4.2 mmolar. Expressed in weight equivalents, the methods described herein include contacting alpha-ketoglutaric acid with a water mixture of potassium bicarbonate, where the water mixture contains from about 0.12 to about 0.42 weight equivalents of potassium bicarbonate per one weight equivalent of water.

Illustratively, the methods described herein include contacting alpha-ketoglutaric acid with a water mixture of sodium carbonate or potassium carbonate, where the water mixture contains from about 1.2 to about 4.2 mmole equivalents of sodium or potassium ions per mL of water, or a sodium or potassium ion concentration range of about 1.2 to about 4.2 mmolar. It is to be understood that sodium carbonate includes two sodium ions, and therefore, expressed in weight equivalents, the methods described herein include contacting alpha-ketoglutaric acid with a water mixture of sodium carbonate, where the water mixture contains from about 0.06 to about 0.22 weight equivalents of sodium carbonate per one weight equivalent of water. It is also to be understood that potassium carbonate includes two potassium ions, and therefore, expressed in weight equivalents, the methods described herein include contacting alpha-ketoglutaric acid with a water mixture of potassium carbonate, where the water mixture contains from about 0.08 to about 0.29 weight equivalents of potassium carbonate per one weight equivalent of water.

Alkali Metal Salts

In some embodiments, the alkali metal salt is selected from lithium bicarbonate, lithium carbonate, sodium bicarbonate sodium carbonate, potassium bicarbonate, and potassium carbonate, and combinations thereof. In some embodiments, the alkali metal salt comprises sodium bicarbonate. In some embodiments, the alkali metal salt comprises sodium carbonate. In some embodiments, the alkali metal salt is sodium bicarbonate. In some embodiments, the alkali metal salt is sodium carbonate.

Ratio of Alkali Metal Salts to Water

In some embodiments, the alkali metal salt and water are added as a mixture. In some embodiments, the alkali metal salt and water mixture contains from 0.1 to 0.35 weight equivalents of alkali metal salt per one weight equivalent of water.

In some embodiments, the sodium bicarbonate and water are added as a mixture. In some embodiments, the sodium bicarbonate and water mixture contains from 0.1 to 0.3 weight equivalents of sodium bicarbonate per one weight equivalent of water. In some embodiments, the sodium bicarbonate and water mixture contains from 0.1 to 0.25 weight equivalents of sodium bicarbonate per one weight equivalent of water. In some embodiments, the sodium bicarbonate and water mixture contains from 0.15 to 0.3 weight equivalents of sodium bicarbonate per one weight equivalent of water. In some embodiments, the sodium bicarbonate and water mixture contains from 0.15 to 0.25 weight equivalents of sodium bicarbonate per one weight equivalent of water. In some embodiments, the sodium bicarbonate and water mixture contains from 0.2 to 0.3 weight equivalents of sodium bicarbonate per one weight equivalent of water. In some embodiments, the sodium bicarbonate and water mixture contains from 0.2 to 0.25 weight equivalents of sodium bicarbonate per one weight equivalent of water. In some embodiments, the sodium bicarbonate and water mixture contains 0.15 weight equivalents of sodium bicarbonate per one weight equivalent of water. In some embodiments, the sodium bicarbonate and water mixture contains 0.16 weight equivalents of sodium bicarbonate per one weight equivalent of water. In some embodiments, the sodium bicarbonate and water mixture contains 0.17 weight equivalents of sodium bicarbonate per one weight equivalent of water. In some embodiments, the sodium bicarbonate and water mixture contains 0.18 weight equivalents of sodium bicarbonate per one weight equivalent of water. In some embodiments, the sodium bicarbonate and water mixture contains 0.19 weight equivalents of sodium bicarbonate per one weight equivalent of water. In some embodiments, the sodium bicarbonate and water mixture contains 0.2 weight equivalents of sodium bicarbonate per one weight equivalent of water. In some embodiments, the sodium bicarbonate and water mixture contains 0.21 weight equivalents of sodium bicarbonate per one weight equivalent of water. In some embodiments, the sodium bicarbonate and water mixture contains 0.22 weight equivalents of sodium bicarbonate per one weight equivalent of water. In some embodiments, the sodium bicarbonate and water mixture contains 0.23 weight equivalents of sodium bicarbonate per one weight equivalent of water. In some embodiments, the sodium bicarbonate and water mixture contains 0.24 weight equivalents of sodium bicarbonate per one weight equivalent of water. In some embodiments, the sodium bicarbonate and water mixture contains 0.25 weight equivalents of sodium bicarbonate per one weight equivalent of water. In some embodiments, the sodium bicarbonate and water mixture contains 0.26 weight equivalents of sodium bicarbonate per one weight equivalent of water. In some embodiments, the sodium bicarbonate and water mixture contains 0.27 weight equivalents of sodium bicarbonate per one weight equivalent of water. In some embodiments, the sodium bicarbonate and water mixture contains 0.28 weight equivalents of sodium bicarbonate per one weight equivalent of water. In some embodiments, the sodium bicarbonate and water mixture contains 0.29 weight equivalents of sodium bicarbonate per one weight equivalent of water. In some embodiments, the sodium bicarbonate and water mixture contains 0.3 weight equivalents of sodium bicarbonate per one weight equivalent of water. In some embodiments, the sodium bicarbonate and water mixture contains 0.31 weight equivalents of sodium bicarbonate per one weight equivalent of water. In some embodiments, the sodium bicarbonate and water mixture contains 0.32 weight equivalents of sodium bicarbonate per one weight equivalent of water. In some embodiments, the sodium bicarbonate and water mixture contains 0.33 weight equivalents of sodium bicarbonate per one weight equivalent of water. In some embodiments, the sodium bicarbonate and water mixture contains 0.34 weight equivalents of sodium bicarbonate per one weight equivalent of water. In some embodiments, the sodium bicarbonate and water mixture contains 0.35 weight equivalents of sodium bicarbonate per one weight equivalent of water.

In some embodiments, the sodium carbonate and water are added as a mixture. In some embodiments, the sodium carbonate and water mixture contains from about 0.05 to about 0.35 weight equivalents of sodium carbonate per one weight equivalent of water. In some embodiments, the sodium carbonate and water mixture contains from about 0.05 to about 0.2 weight equivalents of sodium carbonate per one weight equivalent of water. In some embodiments, the sodium carbonate and water mixture contains from 0.1 to 0.35 weight equivalents of sodium carbonate per one weight equivalent of water. In some embodiments, the sodium carbonate and water mixture contains from 0.1 to 0.3 weight equivalents of sodium carbonate per one weight equivalent of water. In some embodiments, the sodium carbonate and water mixture contains from 0.1 to 0.25 weight equivalents of sodium carbonate per one weight equivalent of water. In some embodiments, the sodium carbonate and water mixture contains from 0.15 to 0.3 weight equivalents of sodium carbonate per one weight equivalent of water. In some embodiments, the sodium carbonate and water mixture contains from 0.15 to 0.25 weight equivalents of sodium carbonate per one weight equivalent of water. In some embodiments, the sodium carbonate and water mixture contains from 0.2 to 0.3 weight equivalents of sodium carbonate per one weight equivalent of water. In some embodiments, the sodium carbonate and water mixture contains from 0.2 to 0.25 weight equivalents of sodium carbonate per one weight equivalent of water. In some embodiments, the sodium carbonate and water mixture contains 0.15 weight equivalents of sodium carbonate per one weight equivalent of water. In some embodiments, the sodium carbonate and water mixture contains 0.16 weight equivalents of sodium carbonate per one weight equivalent of water. In some embodiments, the sodium carbonate and water mixture contains 0.17 weight equivalents of sodium carbonate per one weight equivalent of water. In some embodiments, the sodium carbonate and water mixture contains 0.18 weight equivalents of sodium carbonate per one weight equivalent of water. In some embodiments, the sodium carbonate and water mixture contains 0.19 weight equivalents of sodium carbonate per one weight equivalent of water. In some embodiments, the sodium carbonate and water mixture contains 0.2 weight equivalents of sodium carbonate per one weight equivalent of water. In some embodiments, the sodium carbonate and water mixture contains 0.21 weight equivalents of sodium carbonate per one weight equivalent of water. In some embodiments, the sodium carbonate and water mixture contains 0.22 weight equivalents of sodium carbonate per one weight equivalent of water. In some embodiments, the sodium carbonate and water mixture contains 0.23 weight equivalents of sodium carbonate per one weight equivalent of water. In some embodiments, the sodium carbonate and water mixture contains 0.24 weight equivalents of sodium carbonate per one weight equivalent of water. In some embodiments, the sodium carbonate and water mixture contains 0.25 weight equivalents of sodium carbonate per one weight equivalent of water.

Ratio of Alpha-Ketoglutaric Acid to Alkali Metal Salts

In some embodiments, the alpha-ketoglutaric acid is from about 0.5 to about 3 weight equivalents per one weight equivalent of alkali metal salt. In some embodiments, the alpha-ketoglutaric acid is from 0.5 to 0.9 weight equivalents per one weight equivalent of alkali metal salt.

In some embodiments, the alpha-ketoglutaric acid is from 0.5 to 0.9 weight equivalents per one weight equivalent of sodium bicarbonate. In some embodiments, the alpha-ketoglutaric acid is from 0.6 to 0.9 weight equivalents per one weight equivalent of sodium bicarbonate. In some embodiments, the alpha-ketoglutaric acid is from 0.7 to 0.9 weight equivalents per one weight equivalent of sodium bicarbonate. In some embodiments, the alpha-ketoglutaric acid is from 0.5 to 0.8 weight equivalents per one weight equivalent of sodium bicarbonate. In some embodiments, the alpha-ketoglutaric acid is from 0.6 to 0.8 weight equivalents per one weight equivalent of sodium bicarbonate. In some embodiments, the alpha-ketoglutaric acid is from 0.7 to 0.8 weight equivalents per one weight equivalent of sodium bicarbonate. In some embodiments, the alpha-ketoglutaric acid is 0.7 weight equivalents per one weight equivalent of sodium bicarbonate. In some embodiments, the alpha-ketoglutaric acid is 0.71 weight equivalents per one weight equivalent of sodium bicarbonate. In some embodiments, the alpha-ketoglutaric acid is 0.72 weight equivalents per one weight equivalent of sodium bicarbonate. In some embodiments, the alpha-ketoglutaric acid is 0.73 weight equivalents per one weight equivalent of sodium bicarbonate. In some embodiments, the alpha-ketoglutaric acid is 0.74 weight equivalents per one weight equivalent of sodium bicarbonate. In some embodiments, the alpha-ketoglutaric acid is 0.75 weight equivalents per one weight equivalent of sodium bicarbonate. In some embodiments, the alpha-ketoglutaric acid is 0.76 weight equivalents per one weight equivalent of sodium bicarbonate. In some embodiments, the alpha-ketoglutaric acid is 0.77 weight equivalents per one weight equivalent of sodium bicarbonate. In some embodiments, the alpha-ketoglutaric acid is 0.78 weight equivalents per one weight equivalent of sodium bicarbonate. In some embodiments, the alpha-ketoglutaric acid is 0.79 weight equivalents per one weight equivalent of sodium bicarbonate. In some embodiments, the alpha-ketoglutaric acid is 0.8 weight equivalents per one weight equivalent of sodium bicarbonate.

In some embodiments, the alpha-ketoglutaric acid is from 0.33 to 0.5 mole equivalents per one mol equivalent of sodium bicarbonate. In some embodiments, the alpha-ketoglutaric acid is from 0.33 to 0.45 mole equivalents per one mol equivalent of sodium bicarbonate. In some embodiments, the alpha-ketoglutaric acid is from 0.35 to 0.45 mole equivalents per one mol equivalent of sodium bicarbonate. In some embodiments, the alpha-ketoglutaric acid is from 0.36 to 0.45 mole equivalents per one mol equivalent of sodium bicarbonate. In some embodiments, the alpha-ketoglutaric acid is from 0.37 to 0.45 mole equivalents per one mol equivalent of sodium bicarbonate. In some embodiments, the alpha-ketoglutaric acid is from 0.38 to 0.45 mole equivalents per one mol equivalent of sodium bicarbonate. In some embodiments, the alpha-ketoglutaric acid is from 0.39 to 0.45 mole equivalents per one mol equivalent of sodium bicarbonate. In some embodiments, the alpha-ketoglutaric acid is from 0.4 to 0.45 mole equivalents per one mole equivalent of sodium bicarbonate. In some embodiments, the alpha-ketoglutaric acid is from 0.35 to 0.44 mole equivalents per one mole equivalent of sodium bicarbonate. In some embodiments, the alpha-ketoglutaric acid is from 0.36 to 0.44 mole equivalents per one mole equivalent of sodium bicarbonate. In some embodiments, the alpha-ketoglutaric acid is from 0.37 to 0.44 mole equivalents per one mole equivalent of sodium bicarbonate. In some embodiments, the alpha-ketoglutaric acid is from 0.38 to 0.44 mole equivalents per one mole equivalent of sodium bicarbonate. In some embodiments, the alpha-ketoglutaric acid is from 0.39 to 0.44 mole equivalents per one mole equivalent of sodium bicarbonate. In some embodiments, the alpha-ketoglutaric acid is from 0.4 to 0.44 mole equivalents per one mole equivalent of sodium bicarbonate. In some embodiments, the alpha-ketoglutaric acid is from 0.35 to 0.43 mole equivalents per one mole equivalent of sodium bicarbonate. In some embodiments, the alpha-ketoglutaric acid is from 0.36 to 0.43 mole equivalents per one mole equivalent of sodium bicarbonate. In some embodiments, the alpha-ketoglutaric acid is from 0.37 to 0.43 mole equivalents per one mole equivalent of sodium bicarbonate. In some embodiments, the alpha-ketoglutaric acid is from 0.38 to 0.43 mole equivalents per one mole equivalent of sodium bicarbonate. In some embodiments, the alpha-ketoglutaric acid is from 0.39 to 0.43 mole equivalents per one mole equivalent of sodium bicarbonate. In some embodiments, the alpha-ketoglutaric acid is from 0.4 to 0.43 mole equivalents per one mole equivalent of sodium bicarbonate. In some embodiments, the alpha-ketoglutaric acid is 0.35 mole equivalents per one mole equivalent of sodium bicarbonate. In some embodiments, the alpha-ketoglutaric acid is 0.36 mole equivalents per one mole equivalent of sodium bicarbonate. In some embodiments, the alpha-ketoglutaric acid is 0.37 mole equivalents per one mole equivalent of sodium bicarbonate. In some embodiments, the alpha-ketoglutaric acid is 0.38 mole equivalents per one mole equivalent of sodium bicarbonate. In some embodiments, the alpha-ketoglutaric acid is 0.39 mole equivalents per one mole equivalent of sodium bicarbonate. In some embodiments, the alpha-ketoglutaric acid is 0.4 mole equivalents per one mole equivalent of sodium bicarbonate. In some embodiments, the alpha-ketoglutaric acid is 0.41 mole equivalents per one mole equivalent of sodium bicarbonate. In some embodiments, the alpha-ketoglutaric acid is 0.42 mole equivalents per one mole equivalent of sodium bicarbonate. In some embodiments, the alpha-ketoglutaric acid is 0.43 mole equivalents per one mole equivalent of sodium bicarbonate. In some embodiments, the alpha-ketoglutaric acid is 0.44 mole equivalents per one mole equivalent of sodium bicarbonate. In some embodiments, the alpha-ketoglutaric acid is 0.45 mole equivalents per one mole equivalent of sodium bicarbonate.

In some embodiments, the alpha-ketoglutaric acid is from 1 to 2.8 weight equivalents per one weight equivalent of alkali metal salt. In some embodiments, the alpha-ketoglutaric acid is from 1 to 2.8 weight equivalents per one weight equivalent of sodium carbonate. In some embodiments, the alpha-ketoglutaric acid is from 0.9 to 1.4 weight equivalents per one weight equivalent of sodium carbonate. In some embodiments, the alpha-ketoglutaric acid is from one to 1.4 weight equivalents per one weight equivalent of sodium carbonate. In some embodiments, the alpha-ketoglutaric acid is from 1.1 to 1.4 weight equivalents per one weight equivalent of sodium carbonate. In some embodiments, the alpha-ketoglutaric acid is from 0.9 to 1.3 weight equivalents per one weight equivalent of sodium carbonate. In some embodiments, the alpha-ketoglutaric acid is from one to 1.3 weight equivalents per one weight equivalent of sodium carbonate. In some embodiments, the alpha-ketoglutaric acid is from 1.1 to 1.3 weight equivalents per one weight equivalent of sodium carbonate. In some embodiments, the alpha-ketoglutaric acid is from 0.9 to 1.2 weight equivalents per one weight equivalent of sodium carbonate. In some embodiments, the alpha-ketoglutaric acid is from one to 1.2 weight equivalents per one weight equivalent of sodium carbonate. In some embodiments, the alpha-ketoglutaric acid is from 1.1 to 1.2 weight equivalents per one weight equivalent of sodium carbonate. In some embodiments, the alpha-ketoglutaric acid is 1.05 weight equivalents per one weight equivalent of sodium carbonate. In some embodiments, the alpha-ketoglutaric acid is 1.06 weight equivalents per one weight equivalent of sodium carbonate. In some embodiments, the alpha-ketoglutaric acid is 1.07 weight equivalents per one weight equivalent of sodium carbonate. In some embodiments, the alpha-ketoglutaric acid is 1.08 weight equivalents per one weight equivalent of sodium carbonate. In some embodiments, the alpha-ketoglutaric acid is 1.09 weight equivalents per one weight equivalent of sodium carbonate. In some embodiments, the alpha-ketoglutaric acid is 1.1 weight equivalents per one weight equivalent of sodium carbonate. In some embodiments, the alpha-ketoglutaric acid is 1.11 weight equivalents per one weight equivalent of sodium carbonate. In some embodiments, the alpha-ketoglutaric acid is 1.12 weight equivalents per one weight equivalent of sodium carbonate. In some embodiments, the alpha-ketoglutaric acid is 1.13 weight equivalents per one weight equivalent of sodium carbonate. In some embodiments, the alpha-ketoglutaric acid is 1.14 weight equivalents per one weight equivalent of sodium carbonate. In some embodiments, the alpha-ketoglutaric acid is 1.15 weight equivalents per one weight equivalent of sodium carbonate. In some embodiments, the alpha-ketoglutaric acid is 1.16 weight equivalents per one weight equivalent of sodium carbonate. In some embodiments, the alpha-ketoglutaric acid is 1.17 weight equivalents per one weight equivalent of sodium carbonate. In some embodiments, the alpha-ketoglutaric acid is 1.18 weight equivalents per one weight equivalent of sodium carbonate. In some embodiments, the alpha-ketoglutaric acid is 1.19 weight equivalents per one weight equivalent of sodium carbonate. In some embodiments, the alpha-ketoglutaric acid is 1.20 weight equivalents per one weight equivalent of sodium carbonate.

In some embodiments, the alpha-ketoglutaric acid is from 0.5 to one mole equivalents per one mol equivalent of sodium carbonate. In some embodiments, the alpha-ketoglutaric acid is from 0.6 to one mole equivalents per one mol equivalent of sodium carbonate. In some embodiments, the alpha-ketoglutaric acid is from 0.7 to one mole equivalents per one mol equivalent of sodium carbonate. In some embodiments, the alpha-ketoglutaric acid is from 0.8 to one mole equivalents per one mol equivalent of sodium carbonate. In some embodiments, the alpha-ketoglutaric acid is from 0.5 to 0.9 mole equivalents per one mol equivalent of sodium carbonate. In some embodiments, the alpha-ketoglutaric acid is from 0.6 to 0.9 mole equivalents per one mol equivalent of sodium carbonate. In some embodiments, the alpha-ketoglutaric acid is from 0.7 to 0.9 mole equivalents per one mol equivalent of sodium carbonate. In some embodiments, the alpha-ketoglutaric acid is from 0.8 to 0.9 mole equivalents per one mol equivalent of sodium carbonate.

In some embodiments, the alpha-ketoglutaric acid is 0.75 mole equivalents per one mole equivalent of sodium carbonate. In some embodiments, the alpha-ketoglutaric acid is 0.76 mole equivalents per one mole equivalent of sodium carbonate. In some embodiments, the alpha-ketoglutaric acid is 0.77 mole equivalents per one mole equivalent of sodium carbonate. In some embodiments, the alpha-ketoglutaric acid is 0.78 mole equivalents per one mole equivalent of sodium carbonate. In some embodiments, the alpha-ketoglutaric acid is 0.79 mole equivalents per one mole equivalent of sodium carbonate. In some embodiments, the alpha-ketoglutaric acid is 0.8 mole equivalents per one mole equivalent of sodium carbonate. In some embodiments, the alpha-ketoglutaric acid is 0.81 mole equivalents per one mole equivalent of sodium carbonate. In some embodiments, the alpha-ketoglutaric acid is 0.82 mole equivalents per one mole equivalent of sodium carbonate. In some embodiments, the alpha-ketoglutaric acid is 0.83 mole equivalents per one mole equivalent of sodium carbonate. In some embodiments, the alpha-ketoglutaric acid is 0.84 mole equivalents per one mole equivalent of sodium carbonate. In some embodiments, the alpha-ketoglutaric acid is 0.85 mole equivalents per one mole equivalent of sodium carbonate. In some embodiments, the alpha-ketoglutaric acid is 0.86 mole equivalents per one mole equivalent of sodium carbonate. In some embodiments, the alpha-ketoglutaric acid is 0.87 mole equivalents per one mole equivalent of sodium carbonate. In some embodiments, the alpha-ketoglutaric acid is 0.88 mole equivalents per one mole equivalent of sodium carbonate. In some embodiments, the alpha-ketoglutaric acid is 0.89 mole equivalents per one mole equivalent of sodium carbonate. In some embodiments, the alpha-ketoglutaric acid is 0.9 mole equivalents per one mole equivalent of sodium carbonate.

Contacting Temperature of Alkali Metal Salts and Alpha-Ketoglutaric Acid

In some embodiments, the alpha-ketoglutaric acid is contacted with the alkali metal salt at about 50° C. or less, about 40° C. or less, about 35° C. or less, about 30° C. or less, or about 25° C. or less. In some embodiments, the alpha-ketoglutaric acid is contacted with the alkali metal salt in the range from about 10° C. to about 50° C., from about 10° C. to about 40° C., from about 10° C. to about 35° C., from about 10° C. to about 30° C., from about 10° C. to about 25° C.

In some embodiments, the alpha-ketoglutaric acid is contacted with the sodium bicarbonate and water mixture at 10° C. to 50° C. In some embodiments, the alpha-ketoglutaric acid is contacted with the sodium bicarbonate and water mixture at 10° C. to 40° C. In some embodiments, the alpha-ketoglutaric acid is contacted with the sodium bicarbonate and water mixture at 10° C. to 35° C. In some embodiments, the alpha-ketoglutaric acid is contacted with the sodium bicarbonate and water mixture at 10° C. to 30° C. In some embodiments, the alpha-ketoglutaric acid is contacted with the sodium bicarbonate and water mixture at 10° C. to 25° C. In some embodiments, the alpha-ketoglutaric acid is contacted with the sodium bicarbonate and water mixture at 15° C. to 50° C. In some embodiments, the alpha-ketoglutaric acid is contacted with the sodium bicarbonate and water mixture at 15° C. to 40° C. In some embodiments, the alpha-ketoglutaric acid is contacted with the sodium bicarbonate and water mixture at 15° C. to 30° C. In some embodiments, the alpha-ketoglutaric acid is contacted with the sodium bicarbonate and water mixture at 20° C. to 50° C. In some embodiments, the alpha-ketoglutaric acid is contacted with the sodium bicarbonate and water mixture at 20° C. to 40° C. In some embodiments, the alpha-ketoglutaric acid is contacted with the sodium bicarbonate and water mixture at 20° C. to 35° C. In some embodiments, the alpha-ketoglutaric acid is contacted with the sodium bicarbonate and water mixture at 20° C. to 30° C. In some embodiments, the alpha-ketoglutaric acid is contacted with the sodium bicarbonate and water mixture at 20° C. to 25° C. In some embodiments, the alpha-ketoglutaric acid is contacted with the sodium bicarbonate and water mixture at 25° C. to 50° C. In some embodiments, the alpha-ketoglutaric acid is contacted with the sodium bicarbonate and water mixture at 25° C. to 40° C. In some embodiments, the alpha-ketoglutaric acid is contacted with the sodium bicarbonate and water mixture at 25° C. to 35° C. In some embodiments, the alpha-ketoglutaric acid is contacted with the sodium bicarbonate and water mixture at 25° C. to 30° C. In some embodiments, the alpha-ketoglutaric acid is contacted with the sodium bicarbonate and water mixture at 20° C. In some embodiments, the alpha-ketoglutaric acid is contacted with the sodium bicarbonate and water mixture at 21° C. In some embodiments, the alpha-ketoglutaric acid is contacted with the sodium bicarbonate and water mixture at 22° C. In some embodiments, the alpha-ketoglutaric acid is contacted with the sodium bicarbonate and water mixture at 23° C. In some embodiments, the alpha-ketoglutaric acid is contacted with the sodium bicarbonate and water mixture at 24° C. In some embodiments, the alpha-ketoglutaric acid is contacted with the sodium bicarbonate and water mixture at 25° C. In some embodiments, the alpha-ketoglutaric acid is contacted with the sodium bicarbonate and water mixture at 26° C. In some embodiments, the alpha-ketoglutaric acid is contacted with the sodium bicarbonate and water mixture at 27° C. In some embodiments, the alpha-ketoglutaric acid is contacted with the sodium bicarbonate and water mixture at 28° C. In some embodiments, the alpha-ketoglutaric acid is contacted with the sodium bicarbonate and water mixture at 29° C. In some embodiments, the alpha-ketoglutaric acid is contacted with the sodium bicarbonate and water mixture at 30° C.

In some embodiments, the alpha-ketoglutaric acid is contacted with the sodium carbonate and water mixture at 10° C. to 50° C. In some embodiments, the alpha-ketoglutaric acid is contacted with the sodium carbonate and water mixture at 10° C. to 40° C. In some embodiments, the alpha-ketoglutaric acid is contacted with the sodium carbonate and water mixture at 10° C. to 35° C. In some embodiments, the alpha-ketoglutaric acid is contacted with the sodium carbonate and water mixture at 10° C. to 30° C. In some embodiments, the alpha-ketoglutaric acid is contacted with the sodium carbonate and water mixture at 10° C. to 25° C. In some embodiments, the alpha-ketoglutaric acid is contacted with the sodium carbonate and water mixture at 15° C. to 50° C. In some embodiments, the alpha-ketoglutaric acid is contacted with the sodium carbonate and water mixture at 15° C. to 40° C. In some embodiments, the alpha-ketoglutaric acid is contacted with the sodium carbonate and water mixture at 15° C. to 30° C. In some embodiments, the alpha-ketoglutaric acid is contacted with the sodium carbonate and water mixture at 20° C. to 50° C. In some embodiments, the alpha-ketoglutaric acid is contacted with the sodium carbonate and water mixture at 20° C. to 40° C. In some embodiments, the alpha-ketoglutaric acid is contacted with the sodium carbonate and water mixture at 20° C. to 35° C. In some embodiments, the alpha-ketoglutaric acid is contacted with the sodium carbonate and water mixture at 20° C. to 30° C. In some embodiments, the alpha-ketoglutaric acid is contacted with the sodium carbonate and water mixture at 20° C. to 25° C. In some embodiments, the alpha-ketoglutaric acid is contacted with the sodium carbonate and water mixture at 25° C. to 50° C. In some embodiments, the alpha-ketoglutaric acid is contacted with the sodium carbonate and water mixture at 25° C. to 40° C. In some embodiments, the alpha-ketoglutaric acid is contacted with the sodium carbonate and water mixture at 25° C. to 35° C. In some embodiments, the alpha-ketoglutaric acid is contacted with the sodium carbonate and water mixture at 25° C. to 30° C. In some embodiments, the alpha-ketoglutaric acid is contacted with the sodium carbonate and water mixture at 20° C. In some embodiments, the alpha-ketoglutaric acid is contacted with the sodium carbonate and water mixture at 21° C. In some embodiments, the alpha-ketoglutaric acid is contacted with the sodium carbonate and water mixture at 22° C. In some embodiments, the alpha-ketoglutaric acid is contacted with the sodium carbonate and water mixture at 23° C. In some embodiments, the alpha-ketoglutaric acid is contacted with the sodium carbonate and water mixture at 24° C. In some embodiments, the alpha-ketoglutaric acid is contacted with the sodium carbonate and water mixture at 25° C. In some embodiments, the alpha-ketoglutaric acid is contacted with the sodium carbonate and water mixture at 26° C. In some embodiments, the alpha-ketoglutaric acid is contacted with the sodium carbonate and water mixture at 27° C. In some embodiments, the alpha-ketoglutaric acid is contacted with the sodium carbonate and water mixture at 28° C. In some embodiments, the alpha-ketoglutaric acid is contacted with the sodium carbonate and water mixture at 29° C. In some embodiments, the alpha-ketoglutaric acid is contacted with the sodium carbonate and water mixture at 30° C.

Contacting Time of Alpha-Ketoglutaric Acid with Alkali Metal Salts

In some embodiments, the alpha-ketoglutaric acid and the alkali metal salt and water mixture is stirred for at least 30 min, at least about 1 hour, at least about 2 hours, at least about 3 hours, or at least about 4 hours.

In some embodiments, the alpha-ketoglutaric acid and the sodium bicarbonate and water mixture is stirred for 30 min. In some embodiments, the alpha-ketoglutaric acid and the sodium bicarbonate and water mixture is stirred for 1 hour. In some embodiments, the alpha-ketoglutaric acid and the sodium bicarbonate and water mixture is stirred for 2 hours. In some embodiments, the alpha-ketoglutaric acid and the sodium bicarbonate and water mixture is stirred for 3 hours. In some embodiments, the alpha-ketoglutaric acid and the sodium bicarbonate and water mixture is stirred for 4 hours. In some embodiments, the alpha-ketoglutaric acid and the sodium bicarbonate and water mixture is stirred for 6 hours. In some embodiments, the alpha-ketoglutaric acid and the sodium bicarbonate and water mixture is stirred for 8 hours. In some embodiments, the alpha-ketoglutaric acid and the sodium bicarbonate and water mixture is stirred for 10 hours. In some embodiments, the alpha-ketoglutaric acid and the sodium bicarbonate and water mixture is stirred for 12 hours.

In some embodiments, the alpha-ketoglutaric acid and the sodium carbonate and water mixture is stirred for 30 min. In some embodiments, the alpha-ketoglutaric acid and the sodium carbonate and water mixture is stirred for 1 hour. In some embodiments, the alpha-ketoglutaric acid and the sodium carbonate and water mixture is stirred for 2 hours. In some embodiments, the alpha-ketoglutaric acid and the sodium carbonate and water mixture is stirred for 3 hours. In some embodiments, the alpha-ketoglutaric acid and the sodium carbonate and water mixture is stirred for 4 hours. In some embodiments, the alpha-ketoglutaric acid and the sodium carbonate and water mixture is stirred for 6 hours. In some embodiments, the alpha-ketoglutaric acid and the sodium carbonate and water mixture is stirred for 8 hours. In some embodiments, the alpha-ketoglutaric acid and the sodium carbonate and water mixture is stirred for 10 hours. In some embodiments, the alpha-ketoglutaric acid and the sodium carbonate and water mixture is stirred for 12 hours.

Stirring Temperature of Alpha-Ketoglutaric Acid with Alkali Metal Salts

In some embodiments, the alpha-ketoglutaric acid is stirred with the alkali metal salt at about 50° C. or less, about 40° C. or less, about 35° C. or less, about 30° C. or less, or about 25° C. or less.

In some embodiments, the alpha-ketoglutaric acid and the sodium bicarbonate and water mixture is stirred at 10° C. to 50° C. In some embodiments, the alpha-ketoglutaric acid and the sodium bicarbonate and water mixture is stirred at 10° C. to 40° C. In some embodiments, the alpha-ketoglutaric acid is contacted with the sodium bicarbonate and water mixture at 10° C. to 35° C. In some embodiments, the alpha-ketoglutaric acid is contacted with the sodium bicarbonate and water mixture at 10° C. to 30° C. In some embodiments, the alpha-ketoglutaric acid is contacted with the sodium bicarbonate and water mixture at 10° C. to 25° C. In some embodiments, the alpha-ketoglutaric acid and the sodium bicarbonate and water mixture is stirred at 15° C. to 50° C. In some embodiments, the alpha-ketoglutaric acid and the sodium bicarbonate and water mixture is stirred at 15° C. to 40° C. In some embodiments, the alpha-ketoglutaric acid and the sodium bicarbonate and water mixture is stirred at 15° C. to 30° C. In some embodiments, the alpha-ketoglutaric acid is contacted with the sodium bicarbonate and water mixture at 20° C. to 50° C. In some embodiments, the alpha-ketoglutaric acid is contacted with the sodium bicarbonate and water mixture at 20° C. to 40° C. In some embodiments, the alpha-ketoglutaric acid is contacted with the sodium bicarbonate and water mixture at 20° C. to 35° C. In some embodiments, the alpha-ketoglutaric acid is contacted with the sodium bicarbonate and water mixture at 20° C. to 30° C. In some embodiments, the alpha-ketoglutaric acid is contacted with the sodium bicarbonate and water mixture at 20° C. to 25° C. In some embodiments, the alpha-ketoglutaric acid is contacted with the sodium bicarbonate and water mixture at 25° C. to 50° C. In some embodiments, the alpha-ketoglutaric acid is contacted with the sodium bicarbonate and water mixture at 25° C. to 40° C. In some embodiments, the alpha-ketoglutaric acid is contacted with the sodium bicarbonate and water mixture at 25° C. to 35° C. In some embodiments, the alpha-ketoglutaric acid is contacted with the sodium bicarbonate and water mixture at 25° C. to 30° C. In some embodiments, the alpha-ketoglutaric acid and the sodium bicarbonate and water mixture is stirred at 20° C. In some embodiments, the alpha-ketoglutaric acid and the sodium bicarbonate and water mixture is stirred at 21° C. In some embodiments, the alpha-ketoglutaric acid and the sodium bicarbonate and water mixture is stirred at 22° C. In some embodiments, the alpha-ketoglutaric acid and the sodium bicarbonate and water mixture is stirred at 23° C. In some embodiments, the alpha-ketoglutaric acid and the sodium bicarbonate and water mixture is stirred at 24° C. In some embodiments, the alpha-ketoglutaric acid and the sodium bicarbonate and water mixture is stirred at 25° C. In some embodiments, the alpha-ketoglutaric acid and the sodium bicarbonate and water mixture is stirred at 26° C. In some embodiments, the alpha-ketoglutaric acid and the sodium bicarbonate and water mixture is stirred at 27° C. In some embodiments, the alpha-ketoglutaric acid and the sodium bicarbonate and water mixture is stirred at 28° C. In some embodiments, the alpha-ketoglutaric acid and the sodium bicarbonate and water mixture is stirred at 29° C. In some embodiments, the alpha-ketoglutaric acid and the sodium bicarbonate and water mixture is stirred at 30° C.

In some embodiments, the alpha-ketoglutaric acid and the sodium carbonate and water mixture is stirred at 10° C. to 50° C. In some embodiments, the alpha-ketoglutaric acid and the sodium carbonate and water mixture is stirred at 10° C. to 40° C. In some embodiments, the alpha-ketoglutaric acid is contacted with the sodium carbonate and water mixture at 10° C. to 35° C. In some embodiments, the alpha-ketoglutaric acid is contacted with the sodium carbonate and water mixture at 10° C. to 30° C. In some embodiments, the alpha-ketoglutaric acid is contacted with the sodium carbonate and water mixture at 10° C. to 25° C. In some embodiments, the alpha-ketoglutaric acid and the sodium carbonate and water mixture is stirred at 15° C. to 50° C. In some embodiments, the alpha-ketoglutaric acid and the sodium carbonate and water mixture is stirred at 15° C. to 40° C. In some embodiments, the alpha-ketoglutaric acid and the sodium carbonate and water mixture is stirred at 15° C. to 30° C. In some embodiments, the alpha-ketoglutaric acid is contacted with the sodium carbonate and water mixture at 20° C. to 50° C. In some embodiments, the alpha-ketoglutaric acid is contacted with the sodium carbonate and water mixture at 20° C. to 40° C. In some embodiments, the alpha-ketoglutaric acid is contacted with the sodium carbonate and water mixture at 20° C. to 35° C. In some embodiments, the alpha-ketoglutaric acid is contacted with the sodium carbonate and water mixture at 20° C. to 30° C. In some embodiments, the alpha-ketoglutaric acid is contacted with the sodium carbonate and water mixture at 20° C. to 25° C. In some embodiments, the alpha-ketoglutaric acid is contacted with the sodium carbonate and water mixture at 25° C. to 50° C. In some embodiments, the alpha-ketoglutaric acid is contacted with the sodium carbonate and water mixture at 25° C. to 40° C. In some embodiments, the alpha-ketoglutaric acid is contacted with the sodium carbonate and water mixture at 25° C. to 35° C. In some embodiments, the alpha-ketoglutaric acid is contacted with the sodium carbonate and water mixture at 25° C. to 30° C. In some embodiments, the alpha-ketoglutaric acid and the sodium carbonate and water mixture is stirred at 20° C. In some embodiments, the alpha-ketoglutaric acid and the sodium carbonate and water mixture is stirred at 21° C. In some embodiments, the alpha-ketoglutaric acid and the sodium carbonate and water mixture is stirred at 22° C. In some embodiments, the alpha-ketoglutaric acid and the sodium carbonate and water mixture is stirred at 23° C. In some embodiments, the alpha-ketoglutaric acid and the sodium carbonate and water mixture is stirred at 24° C. In some embodiments, the alpha-ketoglutaric acid and the sodium carbonate and water mixture is stirred at 25° C. In some embodiments, the alpha-ketoglutaric acid and the sodium carbonate and water mixture is stirred at 26° C. In some embodiments, the alpha-ketoglutaric acid and the sodium carbonate and water mixture is stirred at 27° C. In some embodiments, the alpha-ketoglutaric acid and the sodium carbonate and water mixture is stirred at 28° C. In some embodiments, the alpha-ketoglutaric acid and the sodium carbonate and water mixture is stirred at 29° C. In some embodiments, the alpha-ketoglutaric acid and the sodium carbonate and water mixture is stirred at 30° C.

pH

In some embodiments, the alpha-ketoglutaric acid and alkali metal salt and water mixture is stirred until a reaction pH is at least about 6, at least about 6.5, at least about 7, at least about 7.5, at least about 8, at least about 8.5, at least about 9, or in the range from about 6.5 to about 9.

In some embodiments, the alpha-ketoglutaric acid and the sodium bicarbonate and water mixture is stirred until a reaction pH is from 6 to 10. In some embodiments, a pH is from 7 to 9. In some embodiments, a pH is from 7 to 8. In some embodiments, a pH is 7.4±0.4. In some embodiments, a pH is 7.1. In some embodiments, a pH is 7.2. In some embodiments, a pH is 7.3. In some embodiments, a pH is 7.4. In some embodiments, a pH is 7.5. In some embodiments, a pH is 7.6. In some embodiments, a pH is 7.7. In some embodiments, a pH is 7.8. In some embodiments, a pH is 7.9. In some embodiments, a pH is 8.

In some embodiments, the alpha-ketoglutaric acid and the sodium carbonate and water mixture is stirred until a reaction pH is from 6 to 10. In some embodiments, a pH is from 7 to 9. In some embodiments, a pH is from 7 to 8. In some embodiments, a pH is 7.4±0.4. In some embodiments, a pH is 7.1. In some embodiments, a pH is 7.2. In some embodiments, a pH is 7.3. In some embodiments, a pH is 7.4. In some embodiments, a pH is 7.5. In some embodiments, a pH is 7.6. In some embodiments, a pH is 7.7. In some embodiments, a pH is 7.8. In some embodiments, a pH is 7.9. In some embodiments, a pH is 8.

Calcium Salts

In some embodiments, the calcium salt is selected from commercially available calcium salts, including but not limited to calcium format, calcium acetate, calcium chloride, and the like, and mixtures thereof. In some embodiments, the calcium salt is selected from the group consisting of calcium acetate and calcium chloride. In some embodiments, the calcium salt is calcium acetate. In some embodiments, the calcium salt is calcium chloride.

Ratio of Calcium Salts to Water

In some embodiment, the calcium salt and water are added as a mixture. In some embodiments, the calcium salt and water mixture contains from 0.1 to 1 weight equivalents of the calcium salt per one weight equivalent of water. In some embodiments, the calcium salt and water mixture contains from 0.1 to 0.8 weight equivalents of the calcium salt per one weight equivalent of water. In some embodiments, the calcium salt and water mixture contains from 0.1 to 0.6 weight equivalents of the calcium salt per one weight equivalent of water. In some embodiments, the calcium salt and water mixture contains from 0.1 to 0.5 weight equivalents of the calcium salt per one weight equivalent of water. In some embodiments, the calcium salt and water mixture contains from 0.3 to 1 weight equivalents of the calcium salt per one weight equivalent of water. In some embodiments, the calcium salt and water mixture contains from 0.3 to 0.8 weight equivalents of the calcium salt per one weight equivalent of water. In some embodiments, the calcium salt and water mixture contains from 0.3 to 0.6 weight equivalents of the calcium salt per one weight equivalent of water. In some embodiments, the calcium salt and water mixture contains from 0.3 to 0.5 weight equivalents of the calcium salt per one weight equivalent of water. In some embodiments, the calcium salt and water mixture contains 0.3 weight equivalents of the calcium salt per one weight equivalent of water. In some embodiments, the calcium salt and water mixture contains 0.32 weight equivalents of the calcium salt per one weight equivalent of water. In some embodiments, the calcium salt and water mixture contains 0.34 weight equivalents of the calcium salt per one weight equivalent of water. In some embodiments, the calcium salt and water mixture contains 0.36 weight equivalents of the calcium salt per one weight equivalent of water. In some embodiments, the calcium salt and water mixture contains 0.38 weight equivalents of the calcium salt per one weight equivalent of water. In some embodiments, the calcium salt and water mixture contains 0.4 weight equivalents of the calcium salt per one weight equivalent of water. In some embodiments, the calcium salt and water mixture contains 0.42 weight equivalents of the calcium salt per one weight equivalent of water. In some embodiments, the calcium salt and water mixture contains 0.44 weight equivalents of the calcium salt per one weight equivalent of water. In some embodiments, the calcium salt and water mixture contains 0.46 weight equivalents of the calcium salt per one weight equivalent of water. In some embodiments, the calcium salt and water mixture contains 0.48 weight equivalents of the calcium salt per one weight equivalent of water. In some embodiments, the calcium salt and water mixture contains 0.5 weight equivalents of the calcium salt per one weight equivalent of water.

Ratio of Calcium Salt to Alpha-Ketoglutaric Acid

In some embodiments, the calcium salt is from 0.5 to 2 weight equivalents per one weight equivalent of alpha-ketoglutaric acid. In some embodiments, the calcium salt is from 0.6 to 1.7 weight equivalents per one weight equivalent of alpha-ketoglutaric acid. In some embodiments, the calcium salt is from 0.7 to 1.4 weight equivalents per one weight equivalent of alpha-ketoglutaric acid. In some embodiments, the calcium salt is from 0.8 to 1.2 weight equivalents per one weight equivalent of alpha-ketoglutaric acid. In some embodiments, the calcium salt is from 0.9 to 1.1 weight equivalents per one weight equivalent of alpha-ketoglutaric acid. In some embodiments, the calcium salt is 0.8 weight equivalents per one weight equivalent of alpha-ketoglutaric acid. In some embodiments, the calcium salt is 0.85 weight equivalents per one weight equivalent of alpha-ketoglutaric acid. In some embodiments, the calcium salt is 0.86 weight equivalents per one weight equivalent of alpha-ketoglutaric acid. In some embodiments, the calcium salt is 0.87 weight equivalents per one weight equivalent of alpha-ketoglutaric acid. In some embodiments, the calcium salt is 0.88 weight equivalents per one weight equivalent of alpha-ketoglutaric acid. In some embodiments, the calcium salt is 0.89 weight equivalents per one weight equivalent of alpha-ketoglutaric acid. In some embodiments, the calcium salt is 0.9 weight equivalents per one weight equivalent of alpha-ketoglutaric acid. In some embodiments, the calcium salt is 0.91 weight equivalents per one weight equivalent of alpha-ketoglutaric acid. In some embodiments, the calcium salt is 0.92 weight equivalents per one weight equivalent of alpha-ketoglutaric acid. In some embodiments, the calcium salt is 0.93 weight equivalents per one weight equivalent of alpha-ketoglutaric acid. In some embodiments, the calcium salt is 0.94 weight equivalents per one weight equivalent of alpha-ketoglutaric acid. In some embodiments, the calcium salt is 0.95 weight equivalents per one weight equivalent of alpha-ketoglutaric acid. In some embodiments, the calcium salt is 0.96 weight equivalents per one weight equivalent of alpha-ketoglutaric acid. In some embodiments, the calcium salt is 0.97 weight equivalents per one weight equivalent of alpha-ketoglutaric acid. In some embodiments, the calcium salt is 0.98 weight equivalents per one weight equivalent of alpha-ketoglutaric acid. In some embodiments, the calcium salt is 0.99 weight equivalents per one weight equivalent of alpha-ketoglutaric acid. In some embodiments, the calcium salt is 1 weight equivalent per one weight equivalent of alpha-ketoglutaric acid. In some embodiments, the calcium salt is 1.01 weight equivalents per one weight equivalent of alpha-ketoglutaric acid. In some embodiments, the calcium salt is 1.02 weight equivalents per one weight equivalent of alpha-ketoglutaric acid. In some embodiments, the calcium salt is 1.03 weight equivalents per one weight equivalent of alpha-ketoglutaric acid. In some embodiments, the calcium salt is 1.04 weight equivalents per one weight equivalent of alpha-ketoglutaric acid. In some embodiments, the calcium salt is 1.05 weight equivalents per one weight equivalent of alpha-ketoglutaric acid. In some embodiments, the calcium salt is 1.06 weight equivalents per one weight equivalent of alpha-ketoglutaric acid. In some embodiments, the calcium salt is 1.07 weight equivalents per one weight equivalent of alpha-ketoglutaric acid. In some embodiments, the calcium salt is 1.08 weight equivalents per one weight equivalent of alpha-ketoglutaric acid. In some embodiments, the calcium salt is 1.09 weight equivalents per one weight equivalent of alpha-ketoglutaric acid. In some embodiments, the calcium salt is 1.1 weight equivalents per one weight equivalent of alpha-ketoglutaric acid. In some embodiments, the calcium salt is 1.2 weight equivalents per one weight equivalent of alpha-ketoglutaric acid.

In some embodiments, the calcium salt is from 1 to 3 mole equivalents per one mole equivalent of alpha-ketoglutaric acid. In some embodiments, the calcium salt is from 1 to 2 mole equivalents per one mole equivalent of alpha-ketoglutaric acid. In some embodiments, the calcium salt is from 1 to 1.75 mole equivalents per one mole equivalent of alpha-ketoglutaric acid. In some embodiments, the calcium salt is from 1 to 1.5 mole equivalents per one mole equivalent of alpha-ketoglutaric acid. In some embodiments, the calcium salt is from 1.1 to 1.75 mole equivalents per one mole equivalent of alpha-ketoglutaric acid. In some embodiments, the calcium salt is from 1.1 to 1.5 mole equivalents per one mole equivalent of alpha-ketoglutaric acid. In some embodiments, the calcium salt is from 1.1 to 1.3 mole equivalents per one mole equivalent of alpha-ketoglutaric acid. In some embodiments, the calcium salt is from 1.2 to 1.75 mole equivalents per one mole equivalent of alpha-ketoglutaric acid. In some embodiments, the calcium salt is from 1.2 to 1.5 mole equivalents per one mole equivalent of alpha-ketoglutaric acid. In some embodiments, the calcium salt is from 1.2 to 1.3 mole equivalents per one mole equivalent of alpha-ketoglutaric acid. In some embodiments, the calcium salt is one mole equivalent per one mole equivalent of alpha-ketoglutaric acid. In some embodiments, the calcium salt is 1.1 mole equivalents per one mole equivalent of alpha-ketoglutaric acid. In some embodiments, the calcium salt is 1.15 mole equivalents per one mole equivalent of alpha-ketoglutaric acid. In some embodiments, the calcium salt is 1.16 mole equivalents per one mole equivalent of alpha-ketoglutaric acid. In some embodiments, the calcium salt is 1.17 mole equivalents per one mole equivalent of alpha-ketoglutaric acid. In some embodiments, the calcium salt is 1.18 mole equivalents per one mole equivalent of alpha-ketoglutaric acid. In some embodiments, the calcium salt is 1.19 mole equivalents per one mole equivalent of alpha-ketoglutaric acid. In some embodiments, the calcium salt is 1.2 mole equivalents per one mole equivalent of alpha-ketoglutaric acid. In some embodiments, the calcium salt is 1.21 mole equivalents per one mole equivalent of alpha-ketoglutaric acid. In some embodiments, the calcium salt is 1.22 mole equivalents per one mole equivalent of alpha-ketoglutaric acid. In some embodiments, the calcium salt is 1.23 mole equivalents per one mole equivalent of alpha-ketoglutaric acid. In some embodiments, the calcium salt is 1.24 mole equivalents per one mole equivalent of alpha-ketoglutaric acid. In some embodiments, the calcium salt is 1.25 mole equivalents per one mole equivalent of alpha-ketoglutaric acid. In some embodiments, the calcium salt is 1.26 mole equivalents per one mole equivalent of alpha-ketoglutaric acid. In some embodiments, the calcium salt is 1.27 mole equivalents per one mole equivalent of alpha-ketoglutaric acid. In some embodiments, the calcium salt is 1.28 mole equivalents per one mole equivalent of alpha-ketoglutaric acid. In some embodiments, the calcium salt is 1.29 mole equivalents per one mole equivalent of alpha-ketoglutaric acid. In some embodiments, the calcium salt is 1.3 mole equivalents per one mole equivalent of alpha-ketoglutaric acid. In some embodiments, the calcium salt is 1.31 mole equivalents per one mole equivalent of alpha-ketoglutaric acid. In some embodiments, the calcium salt is 1.32 mole equivalents per one mole equivalent of alpha-ketoglutaric acid. In some embodiments, the calcium salt is 1.33 mole equivalents per one mole equivalent of alpha-ketoglutaric acid. In some embodiments, the calcium salt is 1.34 mole equivalents per one mole equivalent of alpha-ketoglutaric acid. In some embodiments, the calcium salt is 1.35 mole equivalents per one mole equivalent of alpha-ketoglutaric acid. In some embodiments, the calcium salt is 1.36 mole equivalents per one mole equivalent of alpha-ketoglutaric acid. In some embodiments, the calcium salt is 1.37 mole equivalents per one mole equivalent of alpha-ketoglutaric acid. In some embodiments, the calcium salt is 1.38 mole equivalents per one mole equivalent of alpha-ketoglutaric acid. In some embodiments, the calcium salt is 1.39 mole equivalents per one mole equivalent of alpha-ketoglutaric acid. In some embodiments, the calcium salt is 1.4 mole equivalents per one mole equivalent of alpha-ketoglutaric acid. In some embodiments, the calcium salt is 1.41 mole equivalents per one mole equivalent of alpha-ketoglutaric acid. In some embodiments, the calcium salt is 1.42 mole equivalents per one mole equivalent of alpha-ketoglutaric acid. In some embodiments, the calcium salt is 1.43 mole equivalents per one mole equivalent of alpha-ketoglutaric acid. In some embodiments, the calcium salt is 1.44 mole equivalents per one mole equivalent of alpha-ketoglutaric acid. In some embodiments, the calcium salt is 1.45 mole equivalents per one mole equivalent of alpha-ketoglutaric acid. In some embodiments, the calcium salt is 1.5 mole equivalents per one mole equivalent of alpha-ketoglutaric acid. In some embodiments, the calcium salt is 1.6 mole equivalents per one mole equivalent of alpha-ketoglutaric acid. In some embodiments, the calcium salt is 1.7 mole equivalents per one mole equivalent of alpha-ketoglutaric acid. In some embodiments, the calcium salt is 1.8 mole equivalents per one mole equivalent of alpha-ketoglutaric acid. In some embodiments, the calcium salt is 1.9 mole equivalents per one mole equivalent of alpha-ketoglutaric acid. In some embodiments, the calcium salt is 2 mole equivalents per one mole equivalent of alpha-ketoglutaric acid.

Contacting Temperature of Bis Salt of AKG with Calcium Salts

In some embodiments, the alpha-ketoglutaric acid is contacted with the calcium salt at about 40° C. or more, about 90° C. or less, or in the range from about 40° C. to about 90° C., or about 65° C. to about 75° C.

In some embodiments, the disodium alpha-ketoglutarate and the calcium salt and water mixture is stirred at 40° C. to 90° C. In some embodiments, the disodium alpha-ketoglutarate and the calcium salt and water mixture is stirred at 50° C. to 80° C. In some embodiments, the disodium alpha-ketoglutarate and the calcium salt and water mixture is stirred at 60° C. to 75° C. In some embodiments, the disodium alpha-ketoglutarate and the calcium salt and water mixture is stirred at 65° C. to 70° C. In some embodiments, the disodium alpha-ketoglutarate and the calcium salt and water mixture is stirred at 60° C. In some embodiments, the disodium alpha-ketoglutarate and the calcium salt and water mixture is stirred at 61° C. In some embodiments, the disodium alpha-ketoglutarate and the calcium salt and water mixture is stirred at 62° C. In some embodiments, the disodium alpha-ketoglutarate and the calcium salt and water mixture is stirred at 63° C. In some embodiments, the disodium alpha-ketoglutarate and the calcium salt and water mixture is stirred at 64° C. In some embodiments, the disodium alpha-ketoglutarate and the calcium salt and water mixture is stirred at 65° C. In some embodiments, the disodium alpha-ketoglutarate and the calcium salt and water mixture is stirred at 66° C. In some embodiments, the disodium alpha-ketoglutarate and the calcium salt and water mixture is stirred at 67° C. In some embodiments, the disodium alpha-ketoglutarate and the calcium salt and water mixture is stirred at 68° C. In some embodiments, the disodium alpha-ketoglutarate and the calcium salt and water mixture is stirred at 69° C. In some embodiments, the disodium alpha-ketoglutarate and the calcium salt and water mixture is stirred at 70° C. In some embodiments, the disodium alpha-ketoglutarate and the calcium salt and water mixture is stirred at 71° C. In some embodiments, the disodium alpha-ketoglutarate and the calcium salt and water mixture is stirred at 72° C. In some embodiments, the disodium alpha-ketoglutarate and the calcium salt and water mixture is stirred at 73° C. In some embodiments, the disodium alpha-ketoglutarate and the calcium salt and water mixture is stirred at 74° C. In some embodiments, the disodium alpha-ketoglutarate and the calcium salt and water mixture is stirred at 75° C. In some embodiments, the disodium alpha-ketoglutarate and the calcium salt and water mixture is stirred at 76° C. In some embodiments, the disodium alpha-ketoglutarate and the calcium salt and water mixture is stirred at 78° C. In some embodiments, the disodium alpha-ketoglutarate and the calcium salt and water mixture is stirred at 80° C.

Contacting Time of Disodium AKG with Ca Salt

In some embodiments, the bis alkali metal salt of alpha-ketoglutaric acid and the calcium salt and water mixture is stirred for at least 30 min, at least about 1 hour, at least about 2 hours, at least about 3 hours, or at least about 4 hours.

In some embodiments, the disodium alpha-ketoglutarate and the calcium salt and water mixture is stirred from 30 min to 24 hours. In some embodiments, the disodium alpha-ketoglutarate and the calcium salt and water mixture is stirred from 1 hour to 12 hours. In some embodiments, the disodium alpha-ketoglutarate and the calcium salt and water mixture is stirred from 4 hours to 9 hours. In some embodiments, the disodium alpha-ketoglutarate and the calcium salt and water mixture is stirred from 5 hours to 6 hours. In some embodiments, the disodium alpha-ketoglutarate and the calcium salt and water mixture is stirred for 4 hours. In some embodiments, the disodium alpha-ketoglutarate and the calcium salt and water mixture is stirred for 5 hours. In some embodiments, the disodium alpha-ketoglutarate and the calcium salt and water mixture is stirred for 6 hours. In some embodiments, the disodium alpha-ketoglutarate and the calcium salt and water mixture is stirred for 8 hours. In some embodiments, the disodium alpha-ketoglutarate and the calcium salt and water mixture is stirred for 10 hours. In some embodiments, the disodium alpha-ketoglutarate and the calcium salt and water mixture is stirred for 12 hours.

Additional Steps of Filtering, Washing, and Drying

In some embodiments, the process further comprises separating the calcium alpha-ketoglutarate. In some embodiments, the separated calcium alpha-ketoglutarate is washed with water. In some embodiments, the separated calcium alpha-ketoglutarate is exposed to a vacuum source. In some embodiments, the separated calcium alpha-ketoglutarate is exposed to a heat source. In some embodiments, the heat source comprises a stream of hot air, an oven, or an IR lamp.

Drying Temperature

In some embodiments, the separated calcium alpha-ketoglutarate is heated to a temperature of at least 30° C. to at least 150° C. In some embodiments, the separated calcium alpha-ketoglutarate is heated to a temperature of at least 50° C. to at least 150° C. In some embodiments, the separated calcium alpha-ketoglutarate is heated to a temperature of at least 60° C. to at least 100° C. In some embodiments, the separated calcium alpha-ketoglutarate is heated to a temperature of at least 70° C. to at least 90° C. In some embodiments, the separated calcium alpha-ketoglutarate is heated to a temperature of at least 80° C. to at least 85° C. In some embodiments, the separated calcium alpha-ketoglutarate is heated to a temperature of at least 50° C. to at least 60° C. In some embodiments, the separated calcium alpha-ketoglutarate is heated to a temperature of at least 50° C. In some embodiments, the separated calcium alpha-ketoglutarate is heated to a temperature of at least 60° C. In some embodiments, the separated calcium alpha-ketoglutarate is heated to a temperature of at least 70° C. In some embodiments, the separated calcium alpha-ketoglutarate is heated to a temperature of at least 80° C. In some embodiments, the separated calcium alpha-ketoglutarate is heated to a temperature of at least 90° C. In some embodiments, the separated calcium alpha-ketoglutarate is heated to a temperature of at least 100° C.

Drying Time

In some embodiments, the separated calcium alpha-ketoglutarate is exposed to the heat source from 1 to 18 hours. In some embodiments, the separated calcium alpha-ketoglutarate is exposed to the heat source from 2 to 15 hours. In some embodiments, the separated calcium alpha-ketoglutarate is exposed to the heat source from 3 to 15 hours. In some embodiments, the separated calcium alpha-ketoglutarate is exposed to the heat source from 4 to 12 hours. In some embodiments, the separated calcium alpha-ketoglutarate is exposed to the heat source from 5 to 10 hours. In some embodiments, the separated calcium alpha-ketoglutarate is exposed to the heat source from 6 to 8 hours. In some embodiments, the separated calcium alpha-ketoglutarate is exposed to the heat source for 2 hours. In some embodiments, the separated calcium alpha-ketoglutarate is exposed to the heat source for 4 hours. In some embodiments, the separated calcium alpha-ketoglutarate is exposed to the heat source for 6 hours. In some embodiments, the separated calcium alpha-ketoglutarate is exposed to the heat source for 8 hours. In some embodiments, the separated calcium alpha-ketoglutarate is exposed to the heat source for 10 hours. In some embodiments, the separated calcium alpha-ketoglutarate is exposed to the heat source for 12 hours.

In another aspect, described herein is a method of making calcium alpha-ketoglutarate, the method comprising the steps of:
  a) contacting alpha-ketoglutaric acid with a sodium bicarbonate and water mixture, thereby forming disodium alpha-ketoglutarate; and
  b) contacting a calcium salt and water mixture with the disodium alpha-ketoglutarate, thereby forming calcium alpha-ketoglutarate;
  wherein the sodium bicarbonate and water mixture contains 0.27 weight equivalents of sodium bicarbonate per one weight equivalent of water;
  wherein the alpha-ketoglutaric acid is 0.74 weight equivalents per one weight equivalent of sodium bicarbonate;
  wherein the alpha-ketoglutaric acid is contacted with the solution of sodium bicarbonate and water at about 10° C. to about 35° C., or at about 10° C. to about 25° C.;
  wherein the alpha-ketoglutaric acid and the solution of sodium bicarbonate and water is stirred for about 2 hours at about 10° C. to about 35° C., or at about 10° C. to about 25° C.;
  wherein the calcium salt is calcium chloride;
  wherein the calcium salt and water mixture contains from 0.2 to about 0.5 weight equivalents of the calcium salt per one weight equivalent of water;
  wherein the calcium salt is 0.95 weight equivalent per one weight equivalent of alpha-ketoglutaric acid;
  wherein the disodium alpha-ketoglutarate and the calcium salt and water mixture is stirred at 65° C. to 70° C.; and
  wherein the disodium alpha-ketoglutarate and the calcium salt and water mixture is stirred for 4 hours.

In another aspect, described herein is a method of making calcium alpha-ketoglutarate, the method comprising the steps of:
  a) contacting alpha-ketoglutaric acid with a sodium carbonate and water mixture, thereby forming disodium alpha-ketoglutarate; and
  b) contacting a calcium salt and water mixture with the disodium alpha-ketoglutarate, thereby forming calcium alpha-ketoglutarate;
  wherein the sodium carbonate and water mixture contains 0.18 weight equivalents of sodium carbonate per one weight equivalent of water;
  wherein the alpha-ketoglutaric acid is 1.14 weight equivalents per one weight equivalent of sodium carbonate;
  wherein the alpha-ketoglutaric acid is contacted with the solution of sodium carbonate and water at about 10° C. to about 35° C., or at about 10° C. to about 25° C.;
  wherein the alpha-ketoglutaric acid and the solution of sodium carbonate and water is stirred for 2 hours at about 10° C. to about 35° C., or at about 10° C. to about 25° C.;
  wherein the calcium salt is calcium chloride;
  wherein the calcium salt and water mixture contains from 0.2 to about 0.5 weight equivalents of the calcium salt per one weight equivalent of water;
  wherein the calcium salt is 0.95 weight equivalent per one weight equivalent of alpha-ketoglutaric acid;
  wherein the disodium alpha-ketoglutarate and the calcium salt and water mixture is stirred at 65° C. to 70° C.; and
  wherein the disodium alpha-ketoglutarate and the calcium salt and water mixture is stirred for 4 hours.

In some embodiments, the methods described herein reduce formation of impurities formed during the process of making Ca-AKG using sodium hydroxide. In some embodiments, the impurity is calcium oxalate and calcium succinate. In some embodiments, the impurity is calcium oxalate. In some embodiments, the impurity is calcium succinate. In some embodiments, the impurity is an unidentified impurity. In some embodiments, the impurity is an unknown impurity.

In another aspect, described herein is a method of making dilithium alpha-ketoglutarate, the method comprising: contacting alpha-ketoglutaric acid and methanol mixture with lithium hydroxide, thereby forming dilithium alpha-ketoglutarate.

In some embodiments, the alpha-ketoglutaric acid and methanol mixture contains from 0.25 to 0.35 weight equivalents of the alpha-ketoglutaric acid per one weight equivalent of methanol. In some embodiments, the alpha-ketoglutaric acid and methanol mixture contains 0.32 weight equivalents of the alpha-ketoglutaric acid per one weight equivalent of methanol. In some embodiments, the alpha-ketoglutaric acid is from 1.6 to 1.7 weight equivalents per one weight equivalent of lithium hydroxide. In some embodiments, the alpha-ketoglutaric acid is 1.66 weight equivalents per one weight equivalent of lithium hydroxide. In some embodiments, the alpha-ketoglutaric acid and methanol mixture and the lithium hydroxide is stirred for 2 to 3 hours. In some embodiments, the alpha-ketoglutaric acid and methanol mixture and the lithium hydroxide is stirred at 50° C. to 55° C.

In another aspect, described herein is a method of making dipotassium alpha-ketoglutarate, the method comprising: contacting alpha-ketoglutaric acid and methanol mixture with potassium hydroxide, thereby forming dipotassium alpha-ketoglutarate.

In some embodiments, the alpha-ketoglutaric acid and methanol mixture contains from 0.25 to 0.35 weight equivalents of the alpha-ketoglutaric acid per one weight equivalent of methanol. In some embodiments, the alpha-ketoglutaric acid and methanol mixture contains 0.32 weight equivalents of the alpha-ketoglutaric acid per one weight equivalent of methanol. In some embodiments, the alpha-ketoglutaric acid is from 1.3 to 1.4 weight equivalents per one weight equivalent of potassium hydroxide. In some embodiments, the alpha-ketoglutaric acid is 1.33 weight equivalents per one weight equivalent of potassium hydroxide. In some embodiments, the alpha-ketoglutaric acid and methanol mixture and the potassium hydroxide is stirred for 2 to 3 hours. In some embodiments, the alpha-ketoglutaric acid and methanol mixture and the potassium hydroxide is stirred at 25° C. to 35° C.

In another aspect, described herein is a method of making zinc alpha-ketoglutarate, the method comprising the steps of:
 a) contacting alpha-ketoglutaric acid and water mixture with a base, thereby forming disodium alpha-ketoglutarate; and
 b) contacting the disodium alpha-ketoglutarate with a zinc salt and water mixture, thereby forming zinc alpha-ketoglutarate.

In some embodiments, the base is sodium hydroxide. In some embodiments, the base is sodium bicarbonate. In some embodiments, the base is sodium carbonate.

In some embodiments, the alpha-ketoglutaric acid and water mixture contains from 0.45 to 0.55 weight equivalents of the alpha-ketoglutaric acid per one weight equivalent of water. In some embodiments, the alpha-ketoglutaric acid and water mixture contains 0.5 weight equivalents of the alpha-ketoglutaric acid per one weight equivalent of water. In some embodiments, the alpha-ketoglutaric acid is from 1.6 to 1.7 weight equivalents per one weight equivalent of sodium hydroxide. In some embodiments, the alpha-ketoglutaric acid is 1.67 weight equivalents per one weight equivalent of sodium hydroxide. In some embodiments, the alpha-ketoglutaric acid is contacted with the sodium hydroxide at 25° C. to 35° C. In some embodiments, the alpha-ketoglutaric acid and the sodium hydroxide is stirred for 2 to 3 hours. In some embodiments, the alpha-ketoglutaric acid and the sodium hydroxide is stirred at 25° C. to 35° C. In some embodiments, the zinc salt is zinc chloride. In some embodiments, the zinc salt and water mixture contains from 0.25 to 0.35 weight equivalents of the zinc salt per one weight equivalent of water. In some embodiments, the zinc salt and water mixture contains 0.3 weight equivalents of the zinc salt per one weight equivalent of water. In some embodiments, the zinc salt is 1.2 weight equivalent per one weight equivalent of alpha-ketoglutaric acid. In some embodiments, the disodium alpha-ketoglutarate and the zinc salt and water mixture is stirred at 80° C. to 85° C. In some embodiments, the disodium alpha-ketoglutarate and the zinc salt and water mixture is stirred for 4 to 5 hours.

INCORPORATION BY REFERENCE

All publications, patents, and patent applications mentioned in this specification are herein incorporated by reference to the same extent as if each individual publication, patent, or patent application was specifically and individually indicated to be incorporated by reference.

Examples

The following examples are provided for illustrative purposes only, and are intended to be purely exemplary of the disclosure and are not intended to limit the scope of the claims provided herein.

Conversion of alpha-ketoglutaric acid to the calcium salt has been previously reported. However, in that process, alpha-ketoglutaric acid is first converted to alpha-ketoglutarate disodium salt using sodium hydroxide, as shown in Scheme 1.

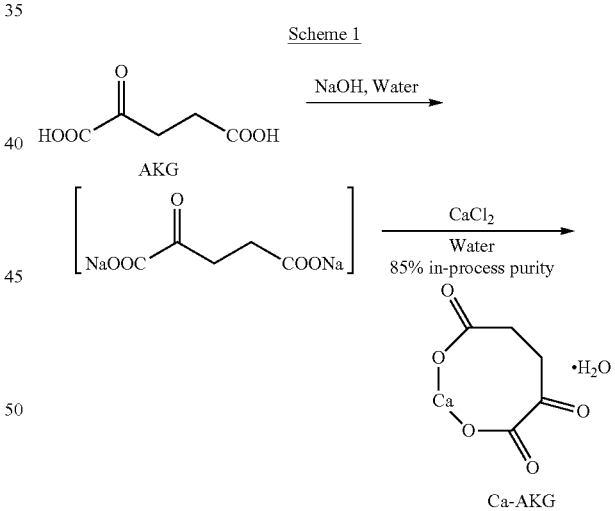

It has been discovered herein that preparation of Ca-AKG under those conditions leads to the formation of impurities. The in-process material can be purified, but only to about 90.3-97.4% (See Examples 1-7). Moreover, the conversion yield only ranged from 55-83 wt/wt %.

It has been discovered that treatment of the Ca-AKG or its hydrates with a solution of 2% HCl can further reduce the impurities and raise the purity to 99.22%. However, a concomitant decrease in yield is also observed.

It has been discovered herein that the impurities were formed during the conversion of alpha-ketoglutaric acid to alpha-ketoglutarate disodium salt. For example, the in-process HPLC sample of Example 7 showed that Ca-AKG was approximately 85% pure.

It was surprisingly found herein that treatment of alpha-ketoglutaric acid with an alkali metal salt not only provided the bis salt of alpha-ketoglutaric acid, but more importantly greatly reduced the formation of impurities found in the isolated Ca-AKG. See Example 8, and Scheme 2. The in-process HPLC sample when using an alkali metal salt such as sodium bicarbonate had a purity of more than 99% indicating, and showing negligible impurity formation. Upon isolation and drying, the Ca-AKG (Example 11) had a purity of 99.3% and the Single Largest Unknown Impurity (SUI) was measured at only 0.46%.

Scheme 2

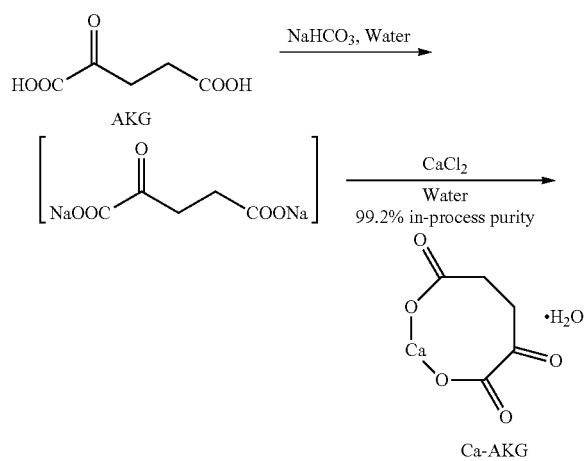

Importantly, it was discovered that the process was fully scalable, and was illustratively repeated on a 50 kg batch (Example 9). The analytical results of Example 8 and Example 9 are similar indicating that scaling the reaction does not lead to an increase in impurities.

Additionally, it was surprisingly found that the yield obtained with the 50 kg batch was actually increased compared to the 500 g batch (from 81.2 to 94.2%). Methods and processes described herein lead to improved isolation without additional purification, resulting in a decrease in plant unit operations thus avoiding product loss (a decrease in yield) and additional cost.

Comparable results are observed for alternative alkali metal salts, such as sodium carbonate. It was found that treatment of alpha-ketoglutaric acid with sodium carbonate also greatly reduced the formation of impurities (See Example 10) found in the isolated Ca-AKG. See Scheme 3.

Scheme 3

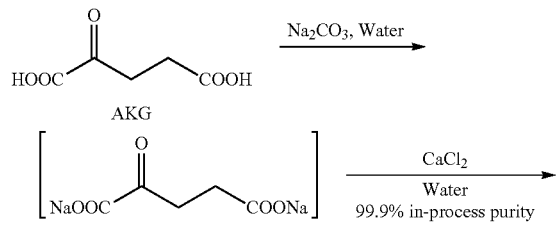

-continued

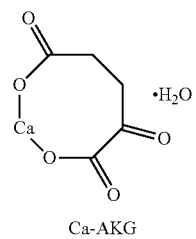

Ca-AKG

Example 1. Synthesis of Ca-AKG using NaOH (250 g scale). Sodium hydroxide (150 g, 3.76 mol) was dissolved in 1000 mL water. alpha-Ketoglutaric acid (250.0 g, 1.71 mol) was added at 25-35° C. The solution was stirred for 2-3 hour at 25-35° C. Calcium chloride (569 g, 5.13 mol, 3.0 eq) dissolved into 1000 mL of water was added to the reaction mass at 25-35° C. The reaction mass was stirred at 65-70° C. for 4-5 hours. The resultant precipitate was collected and washed with 500 mL of water. The solid was dried at 80-90° C. for 6 hours to give 265 g (77% yield).

Example 2. Synthesis of Ca-AKG using NaOH (50 g scale). Sodium hydroxide (30 g, 0.75 mol, 2.2 eq) was dissolved in 200 mL water. alpha-Ketoglutaric acid (50.0 g, 0.342 mol) was added at 25-35° C. The solution was stirred for 2-3 hour at 25-35° C. Calcium chloride (113 g, 1.026 mol, 3.0 eq) dissolved into 200 mL of water was added to the reaction mass at 60-70° C. The reaction mass was stirred at 60-70° C. for 4-5 hours. The resultant precipitate was collected and washed with 100 mL of water. The solid was dried at 70-80° C. for 6-8 hours to give 53.8 g (78% yield).

Example 3. Synthesis of Ca-AKG using NaOH (50 g scale) with reverse addition of $CaCl_2$ (1 equiv). Sodium hydroxide (30 g, 0.75 mol, 2.2 eq) was dissolved in 200 mL water. alpha-Ketoglutaric acid (50.0 g, 0.342 mol) was added at 25-35° C. The solution was stirred for 2-3 hour at 25-35° C. The reaction mass was added to a solution of calcium chloride (38 g, 0.342 mol, 1.0 eq) dissolved into 200 mL of water at 25-35° C. The reaction mass was stirred at 65-70° C. for 4-5 hours. The resultant precipitate was collected and washed with 100 mL of water. The solid was dried at 70-80° C. for 6-8 hours to give 37.9 g (55% yield).

Example 4. Synthesis of Ca-AKG using NaOH (50 g scale) with reverse addition of $CaCl_2$ (2 equiv). Sodium hydroxide (30 g, 0.75 mol 2.2 eq) was dissolved in 200 mL water. alpha-Ketoglutaric acid (50.0 g, 0.342 mol) was added at 25-35° C. The solution was stirred for 2-3 hour at 25-35° C. The reaction mass was added to a solution of calcium chloride (76 g, 0.684 mmol, 2.0 eq) dissolved into 200 mL of water at 25-35° C. The reaction mass was stirred at 65-70° C. for 4-5 hours. The resultant precipitate was collected and washed with 100 mL of water. The solid was dried at 70-80° C. for 6-8 hours to give 55.89 g (81% yield).

Example 5. Synthesis of Ca-AKG using NaOH (100 g scale) with reverse addition of $CaCl_2$ (1.3 equiv). Sodium hydroxide (60 g, 1.5 mol, 2.2 eq was dissolved in 200 mL water. alpha-Ketoglutaric acid (100.0 g, 0.684 mol) was added at 25-35° C. The solution was stirred for 2-3 hour at 25-35° C. The reaction mass was added to a solution of calcium chloride (100 g, 0.903 mol, 1.32 eq) dissolved into 200 mL of water at 25-35° C. The reaction mass was stirred at 65-70° C. for 4-5 hours. The resultant precipitate was collected and washed with 100 mL of water. The solid was dried at 70-80° C. for 6-8 hours to give 103.5 g (75% yield).

Example 6. Synthesis of Ca-AKG using NaOH (500 g scale) with reverse addition of $CaCl_2$ (1.3 equiv). Sodium hydroxide (300, g, 7.53 mol) was dissolved in 1000 mL water. alpha-Ketoglutaric acid (500.0 g, 3.4 mmol) was added at 15-20° C. The solution was stirred for 2-3 hour at 15-20° C. The reaction mass was added to a solution of calcium chloride (500 g, 4.5 mol, 1.32 eq) dissolved into 1000 mL of water at room temperature. The reaction mass was stirred at 80-85° C. for 4-5 hours. The resultant precipitate was collected and washed with 500 mL of water. The solid was dried at 80-85° C. for 6-8 hours to give 579.5 g (84% yield).

Example 7. Synthesis of Ca-AKG using NaOH (100 g scale) with HCl wash. Sodium hydroxide (60 g, 1.50 mol) was dissolved in 200 mL water. alpha-Ketoglutaric acid (100.0 g, 0.684 mol) was added at 15-20° C. The solution was stirred for 2-3 hours at 15-20° C. The reaction mass was added to a solution of calcium chloride (100 g, 0.903 mol, 1.32 eq) dissolved into 200 mL of water at room temperature. The reaction mass was stirred at 80-85° C. for 4-5 hours. The resultant precipitate was collected and washed with 100 mL of water. Wet slurry charge into 2% HCl solution (200 mL), the reaction mass was stirred at 80-85° C. for 1-2 hours. The resultant precipitate was collected and washed with 100 mL of water. The solid was dried at 80-85° C. for 6-8 hours to give 103.5 g (75% yield).

Example 8. Synthesis of Ca-AKG using NaHCO$_3$ (500 g scale). Sodium bicarbonate (690 g, 8.21 mol) was suspended in 3000 mL water. alpha-Ketoglutaric acid (500.0 g, 3.4 mol) was added at 15-20° C. The solution was stirred for 2 hours at 15-20° C. The reaction mass was added to a solution of calcium chloride (500 g, 4.5 mol, 1.32 eq) dissolved into 1000 mL of water at room temperature. The reaction mass was stirred at 65-70° C. for 4-5 hours. The resultant precipitate was collected and washed with 500 mL of water. The solid was dried at 80-85° C. for 6-8 hours to give 558.9 g (81% yield).

Example 9. Synthesis of Ca-AKG using NaHCO$_3$ (50 kg scale). alpha-Ketoglutaric acid (50 kg) was charged to 250 L of water at 25-35° C. Sodium bicarbonate (69 kg) was slowly added to the reaction mass at 25-35° C. The reaction mass was stirred until the reaction pH was (7.4±0.4). The reaction mass was added to a solution of calcium chloride (50 kg) in 125 L water at 25-35° C. The reaction mass as heated at 65-70° C. for 4 hours and then cooled to 45-50° C. The precipitate was collected by filtration and the resultant filter cake was washed with 50 L of water. The cake was combined with 150 L of water and the reaction mass was heated at 65-70° C. for 1 hour then cooled to 45-50° C. The solid was collected by filtration and the filter cake washed with 50 L of water. The cake was dried at 50-60° C. under vacuum until the moisture content was 8.5-10.0% to provide 65 kg of calcium alpha-ketoglutaric acid.

Example 10. Synthesis of Ca-AKG using Na$_2$CO$_3$ (25 g scale). Sodium carbonate (22.0 g, 0.205 mol.) was suspended in 125 mL water. alpha-Ketoglutaric acid (25.0 g, 0.171 mol.) was added at 25-30° C. The solution was stirred for 2 hours at 25-35° C. The reaction mass was added to a solution of calcium chloride (23.7 g, 0.213 mol), dissolved into 100 mL of water at room temperature. The reaction mass was stirred at 65-70° C. for 4-5 hours. The resultant precipitate was collected and washed with 25 mL of water. The wet slurry was charged into 100 mL water, the reaction mass was stirred at 65-70° C. for 1-2 hours. The resultant precipitate was collected and washed with 25 mL of water. The wet slurry was charged into 2% HCl solution (100 mL) and the reaction mass was stirred at 65-70° C. for 1-2 hours. The resultant precipitate was collected and washed with 25 mL of water. The solid was added to 100 mL water and the reaction mass was stirred at 65-70° C. for 1-2 hours. The resultant precipitate was collected and washed with 25 mL of water. The solid was dried at 50-60° C. for 5-6 hours to give 28.0 g (Yield=81.1%).

Example 11. Synthesis of Ca-AKG using NaHCO$_3$ (500 kg scale). alpha-Ketoglutaric acid (499.8 kg, 3421 mol) was dissolved in 2500 L of water at 25-35° C. Sodium bicarbonate (675 kg, 8035 mol) was added the reaction mass over 2-4 hours at 25-35° C. The solution was stirred for 2 hours at 25-35° C. The reaction mass was added to a solution of calcium chloride (475 kg, 4280 mol) dissolved into 1500 mL of water at 25-35° C. The reaction mass was stirred at 65-70° C. for 4 hours. The reaction mass was cooled to 45-55° C. then the participate was collected in an Agitated Nutsche Filter Dryer. The precipitate was stirred in 2500 L of water for 2 hours at 45-55° C. then filtered. The solid was washed with 1000 L of water. The solid is dried at 50-60° C. to provide 651.78 kg of calcium alpha-ketoglutarate monohydrate.

Example 12. Comparison of Impurity Data. Comparison of impurity data for Examples 4, 5, 7, and 11 is given in the following Table 1.

TABLE 1

| HPLCRRT | Example 4 Isolated (2% HCl wash not used) Area % | Example 5 Isolated (2% HCl wash not used) Area % | Example 7 Pre 2% HCl wash Area % | Example 7 Post 2% HCl wash Area % | Example 11 Isolated (2% HCl wash not used) Area % |
|---|---|---|---|---|---|
| 0.55 | 0.08 | 0.11 | 0.20 | ND | ND |
| 0.57 (Ca Oxalate) | 0.40 | 0.06 | 0.13 | 0.05 | ND |
| 1.00 (AKG) | 93.87 | 94.83 | 91.05 | 96.22 | 99.30 |
| 1.37 | ND | ND | ND | ND | 0.08 |
| 1.41 | ND | 0.10 | ND | ND | ND |
| 1.49 (Ca Succinate) | 0.27 | 0.22 | 0.67 | 0.08 | ND |
| 1.74 | 2.21 | 2.42 | 2.42 | 1.85 | 0.46 |
| 1.93 | ND | ND | 0.32 | 0.29 | ND |
| 2.07 | 0.53 | 1.16 | 0.76 | 0.65 | 0.07 |
| 2.15 | 2.44 | 0.96 | 1.88 | 0.26 | 0.06 |
| 2.83 | ND | ND | 0.06 | 0.05 | ND |
| 3.13 | ND | ND | ND | 0.07 | ND |
| 3.26 | ND | ND | 0.07 | 0.05 | ND |
| 3.43 | ND | ND | 0.36 | 0.25 | ND |
| 3.47 | ND | ND | ND | 0.06 | ND |
| 3.55 | 0.07 | ND | 0.14 | 0.08 | ND |

TABLE 1-continued

| HPLCRRT | Example 4 Isolated (2% HCl wash not used) Area % | Example 5 Isolated (2% HCl wash not used) Area % | Example 7 Pre 2% HCl wash Area % | Example 7 Post 2% HCl wash Area % | Example 11 Isolated (2% HCl wash not used) Area % |
|---|---|---|---|---|---|
| 3.79 | ND | 0.06 | ND | ND | ND |
| 4.13 | 0.05 | ND | ND | ND | ND |
| 4.93 | ND | ND | 1.83 | ND | ND | a. Only impurities above ≥0.05% are listed

Related Compounds by HPLC:

Preparation of Buffer: Weigh and transfer about 2.72 g of potassium dihydrogen phosphate in 1000 mL water and dissolve and mix. Add 2.0 mL of orthophosphoric acid to the buffer solution and mix. Filter through 0.45 u or finer porosity membrane filter.

Mobile Phase A: Use buffer and methanol (95:05) v/v.
Mobile Phase B: Use buffer and methanol (50:50) v/v.

Preparation of dilute Hydrochloric acid: Transfer 0.8 mL of Hydrochloric acid to 100 mL volumetric flask containing about 50 mL of cooled water dilute to volume with water and mix.

Preparation of Blank Solution: Accurately transfer 5 mL of dil. HCI in 20 mL volumetric flask and make up with diluent up to the mark.

Preparation of Ca-Succinate stock solution: Accurately weigh and transfer about 5.0 mg of Ca-Succinate in 25 mL volumetric flask, add 10 mL of water and sonicate and mix, add 5 mL of dil. HCI and sonicate to dissolve. Make up the volume with diluent up to the mark and mix.

Preparation of Ca-Oxalate stock solution: Accurately weigh and transfer about 5.0 mg of Ca-Oxalate in 25 mL volumetric flask, add 10 mL of water and sonicate and mix, add 5 mL of dil. HCI and sonicate to dissolve. Make up the volume with diluent up to the mark and mix.

Preparation of COF stock solution: Accurately weigh and transfer about 5.0 mg of COF in 25 mL volumetric flask, add 10 mL of water and sonicate and mix, add 5 mL of dil. HCI and sonicate to dissolve. Make up the volume with diluent up to the mark and mix.

Preparation of System suitability solution: Accurately transfer each 5 mL of Ca-Succinate, Ca-Oxalate and COF stock solutions into 20 mL volumetric flask and make up with diluent and mix.

Preparation of Standard solution: Accurately transfer each 2.5 mL of Ca-Succinate, Ca-Oxalate and COF stock solutions into 20 mL volumetric flask and make up with diluent and mix.

Preparation of sample solution: Accurately weigh and transfer about 100.0 mg of test sample in 20 mL volumetric flask add 10 mL of water and sonicate and mix, add 5 mL of dil. HCI and sonicate to dissolve. Make up the volume with diluent up to the mark and mix.

Procedure: Inject Blank solution (Duplicate) in to the chromatograph and record the chromatogram. Disregard the average blank peak area from known impurities (if any).

Order of injections is as follows:

| Injection Sequence | No of Injection |
|---|---|
| Blank | 2 |
| System Suitability solution | 6 |
| Standard solution | 2 |
| Sample solution | 1 |
| Standard (Bracketing) | 1 |

Evaluation of system suitability: Inject system suitability solution six times in to the chromatograph and record the chromatogram.

Inject standard solution (Duplicate), sample solution in to the chromatograph and record the chromatogram. Disregard blank peaks from the sample chromatogram and calculate the results.

Calculation: Use COF standard Average area and concentration for unknown and Total impurity calculation $$\text{Result (\% w/w)} = \frac{R_u}{R_s} \times \frac{C_s}{C_u} \times P$$

Ru=Peak response of each impurity peak (Known/Individual Unknown/Sum of Total except COF peak) from the sample solution.
Rs=Average area peak response of the corresponding standards from standard solution.
Cu=Concentration of sample solution.
Cs=Concentration of the corresponding standards in the standard solution.
P=Potency corresponding standards Assay by HPLC: (% w/w, as such)

Buffer and dilute hydrochloric acid were prepared as above.

Mobile Phase: Use buffer and methanol (95:05) v/v.

Preparation of Blank solution: take 1 mL of dil. HCI in 10 mL volumetric flask and make up with diluent up to the mark and mix.

Preparation of Standard solution: Accurately weigh and transfer about 100.0 mg of standard in 100 mL volumetric flask add 30 mL of diluent and sonicate and mix, add 10 mL of dil. HCI and sonicate to dissolve. Make up the volume with diluent up to the mark and mix.

Preparation of Sample solution: Accurately weigh and transfer about 100.0 mg of test sample in 100 mL volumetric flask add 30 mL of diluent and sonicate and mix, add 10 mL of dil. HCI and sonicate to dissolve. Make up the volume with diluent up to the mark and mix.

Evaluation of Blank: Inject Blank solution in to the chromatograph and record the chromatogram. No peak should be observed at the retention time of analyte.

Evaluation of system suitability: Inject standard solution five times in to the chromatograph and record the chromatogram.

Procedure: Inject sample solution duplicate into the chromatograph and record the chromatograms.

Order of injections is as follows:

| Order | No of injection |
|---|---|
| Blank | 1 |
| Standard solution | 5 |
| Sample solution | 2 |
| Standard Bracketing | 1 |

$$\text{Assay (\% w/w)} = \frac{AT}{AS} \times \frac{CS}{CT} \times P$$

AT=Average Area of COF peaks in sample solution

AS=Average Area of COF peaks in standard solution

CS=Concentration of standard solution

CT=Concentration of sample solution

P=Potency of COF standard

Calcium alpha-ketoglutarate monohydrate reference standard was prepared as described in Example 13. The analytical results are presented in Table 2, Table 3, Table 4, and Table 5.

Example 13. Synthesis of Calcium alpha-Ketoglutarate Monohydrate Reference Standard Sodium bicarbonate (552 g, 6.57 mol) was dissolved in 2000 mL water. alpha-Ketoglutaric acid (400 g, 2.73 mol) was added at 15-20° C. The solution was stirred for 2 hours at 15-20° C. The reaction mass was added to a solution of calcium chloride (400 g, 3.61 mol) dissolved into 800 mL of water at room temperature. The reaction mass was stirred at 65-70° C. for 4-5 hours. The resultant precipitate was collected and washed with 400 mL of water. The wet slurry was charged into 1200 mL water and heated at 65-70° C. for 1 hour. The reaction mixture was cooled to 40-45° C. Reaction mixture was filtered and wash with 400 mL water. The solid was dried at 50-60° C. for 10 hours to give 501 g (yield: 1.25 w/w).

TABLE 2

Calcium alpha-ketoglutarate Monohydrate Reference Standard

| Test | Results |
|---|---|
| $^1$H NMR | Consistent with structure: See Table 3 |
| $^{13}$C NMR | Consistent with structure: See Table 4 |
| Mass Spectrometry | m/$z_{obs}$ = 145.0 |
| FT-IR | Consistent with structure: See Table 5 |
| Purity by HPLC (% w/w) | 99.22 |
| Calcium oxalate | 0.01 |
| Calcium succinate | Not detected |
| Any unknown individual impurity | 0.35 |
| Total impurities | 0.78 |
| Calcium content(%) | 21.3 |
| Moisture content (% w/w) | 8.55 |
| Chlorides and sulfates | <0.2 |

TABLE 3

$^1$H-NMR Data for Calcium alpha-ketoglutarate Monohydrate Reference Standard

| Sr. No. | Chemical Shift (ppm) | Relative integral | Multiplicity | Coupling Constant | Assignment |
|---|---|---|---|---|---|
| 1 | 2.515 | 2H | t | 6.4 Hz | C(7) H$_2$ |
| 2 | 3085 | 2H | t | 6.8 hz | C(6) H$_2$ |

TABLE 4

$^{13}$C-NMR Data for Calcium alpha-ketoglutarate Monohydrate Reference Standard

| Sr. No. | Chemical Shift (ppm) | Type of Carbon | Assignment |
|---|---|---|---|
| 1. | 30.73 | CH$_2$ | C(6) |
| 2. | 35.61 | CH2 | C(7) |
| 3. | 169.53 | C=O | C(4), C(8) |
| 4. | 181.73 | C=O | C(5) |

TABLE 5

FT-IR Data for Calcium alpha-ketoglutarate Monohydrate Reference Standard

| Absorbance Band (cm$^{-1}$) | Assignment |
|---|---|
| 3501.4 | OH |
| 1703.9 | C=O |
| 1651.3 | C=O |
| 1562.8 | C=O |

Example 14. Synthesis of Dilithium Salt of AKG (Li$_2$-AKG). alpha-Ketoglutaric acid (10.0 g, 0.068 mol) was dissolved in 40 mL methanol. Lithium hydroxide (6.0 g, 0.142 mol) was added to the solution. The solution was stirred for 2.0-3.0 hours at 50-55° C. The resulted precipitate was isolated, and the cake was washed with 10 mL methanol. The solid was dried at 75-80° C. for 5-6 hours to give 7.56 g (70% yield).

Example 15. Synthesis of Dipotassium Salt of AKG (K$_2$-AKG). alpha-Ketoglutaric acid (10.0 g, 0.068 mol) was dissolved in 40 mL methanol, and stirred at ambient temperature to a clear solution. Potassium hydroxide (7.54 g, 0.134 mol) was added to the solution. The solution was stirred for 2.0-3.0 hours at 25-35° C. The resulted precipitate was isolated, and the cake was washed with 10 mL methanol. The solid was dried at 75-85° C. for 5-6 hours to give 7.8 g (52% yield).

Example 16. Synthesis of Zinc Salt of AKG (Zn-AKG). alpha-Ketoglutaric acid (10.0 g, 0.068 mol) was dissolved in 20 mL water. Sodium hydroxide (6.0 g, 0.149 mol) was charged into alpha-ketoglutaric acid solution. The solution was stirred for 2.5-3.0 hours at 25-35° C. Charge zinc chloride solution (12.0 g, 0.088 mol, 1.32 eq. was dissolved into 40 mL water) into reaction mass. After complete addition of zinc chloride solution reaction mass were stirred at 80-85° C. for 4-5 hours. The resultant precipitate was collected and washed with 10 mL of water. The solid was dried at 80-85° C. for 6-8 hours to give 10.2 g (73% yield).

While preferred embodiments of the present disclosure have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the disclosure described herein may be employed in practicing the invention. It is intended that the following claims define the scope of the disclosure and that methods and structures within the scope of these claims and their equivalents be covered thereby.

What is claimed is:

1. A method for making calcium alpha-ketoglutarate, the method comprising:
    a) contacting alpha-ketoglutaric acid with an alkali metal salt selected from the group consisting of lithium, sodium, and potassium salts of bicarbonate, and lithium, sodium, and potassium salts of carbonate, and combinations thereof, thereby forming a bis salt of alpha-ketoglutarate; and
    b) contacting the bis salt of alpha-ketoglutarate with a calcium salt, thereby forming calcium alpha-ketoglutarate.

2. A method for making calcium alpha-ketoglutarate, the method comprising:
    a) contacting alpha-ketoglutaric acid with an alkali metal salt of an acid and water to form a solution having a pH in the range from about 5.0 to about 11.9, where the alkali metal salt is selected from the group consisting of lithium, sodium, and potassium salts of bicarbonate, and lithium, sodium, and potassium salts of carbonate, and combinations thereof, thereby forming a bis salt of alpha-ketoglutarate; and
    b) contacting the bis salt of alpha-ketoglutarate with a calcium salt and water, thereby forming calcium alpha-ketoglutarate.

3. The method of claim 1 wherein the alpha-ketoglutaric acid is mixed with water.

4. The method of claim 3 wherein the alpha-ketoglutaric acid and water mixture is prepared from or contains from about 0.05 to about 0.5 weight equivalents of alpha-ketoglutaric acid per one weight equivalent of water.

5. The method of claim 1 wherein the alkali metal salt is mixed with water.

6. The method of claim 5 wherein the alkali metal salt and water mixture is prepared from or contains from about 0.1 to about 0.35 weight equivalents of alkali metal salt per one weight equivalent of water.

7. The method of claim 1 wherein the alkali metal salt is sodium bicarbonate, sodium carbonate, or a mixture thereof.

8. The method of claim 1 wherein the alkali metal salt is sodium bicarbonate.

9. The method of claim 1 wherein the alkali metal salt is sodium carbonate.

10. The method of claim 1 wherein the alkali metal salt is added to the alpha-ketoglutaric acid to form a mixture having a pH of about 6.5 or greater.

11. The method of claim 1 wherein the alpha-ketoglutaric acid is from about 0.5 to about 3 weight equivalents per one weight equivalent of alkali metal salt.

12. The method of claim 1 wherein the calcium salt is selected from the group consisting of calcium formate, calcium acetate, and calcium chloride.

13. The method of claim 12 wherein the calcium salt is calcium chloride.

14. The method of claim 1 wherein the calcium salt is mixed with water.

15. The method of claim 14 wherein the calcium salt and water mixture is prepared from or contains from about 0.1 to about 1 weight equivalents of the calcium salt per one weight equivalent of water.

16. The method of claim 1 wherein the calcium salt is from 0.5 to 2 weight equivalents per one weight equivalent of alpha-ketoglutaric acid.

17. The method of claim 1 wherein the bis alkali metal salt of the alpha-ketoglutarate is contacted with the calcium salt and water mixture at about 40° C. to about 90° C.

18. The method of claim 1 further comprising drying the calcium alpha-ketoglutarate.

19. The method of claim 18 where the dried calcium alpha-ketoglutarate is about 50% or less calcium alpha-ketoglutarate dihydrate, or about 50% or greater calcium alpha-ketoglutarate monohydrate.

20. The method of claim 2 wherein the alkali metal salt is sodium bicarbonate, sodium carbonate, or a mixture thereof.

* * * * *